(12) United States Patent
Gunasekar et al.

(10) Patent No.: US 11,701,053 B2
(45) Date of Patent: *Jul. 18, 2023

(54) METHOD FOR HOSTING MOBILE ACCESS TO HIGH-RESOLUTION ELECTROENCEPHALOGRAPHY DATA

(71) Applicant: Zeto, Inc., Santa Clara, CA (US)

(72) Inventors: Aswin Gunasekar, Santa Clara, CA (US); Gabor Braun, Salgótarján (HU); Zoltan Nadasdy, Austin, TX (US)

(73) Assignee: Zeto, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/875,341

(22) Filed: Jul. 27, 2022

(65) Prior Publication Data

US 2023/0029127 A1    Jan. 26, 2023

Related U.S. Application Data

(63) Continuation of application No. 16/119,908, filed on Aug. 31, 2018, now Pat. No. 11,432,757.

(60) Provisional application No. 62/553,021, filed on Aug. 31, 2017.

(51) Int. Cl.
| | | |
|---|---|---|
| G06K 11/00 | (2006.01) |
| A61B 5/369 | (2021.01) |
| G16H 40/63 | (2018.01) |
| A61B 5/00 | (2006.01) |
| G16H 40/67 | (2018.01) |
| G16H 30/20 | (2018.01) |
| A61B 5/316 | (2021.01) |

(52) U.S. Cl.
CPC .......... *A61B 5/369* (2021.01); *A61B 5/0006* (2013.01); *A61B 5/316* (2021.01); *A61B 5/6803* (2013.01); *A61B 5/7435* (2013.01); *G06K 11/00* (2013.01); *G16H 30/20* (2018.01); *G16H 40/63* (2018.01); *G16H 40/67* (2018.01)

(58) Field of Classification Search
CPC .................................. G16H 40/63; A61B 5/369
See application file for complete search history.

(56) References Cited

U.S. PATENT DOCUMENTS

| | | | |
|---|---|---|---|
| 2013/0097086 A1* | 4/2013 | Dala | G06Q 10/00 705/51 |
| 2017/0035317 A1* | 2/2017 | Jung | A61B 3/0025 |
| 2019/0059770 A1* | 2/2019 | Gunasekar | G16H 40/67 |

* cited by examiner

*Primary Examiner* — Samantha (Yuehan) Wang
(74) *Attorney, Agent, or Firm* — Run8 Patent Group, LLC; Peter Miller

(57) ABSTRACT

One variation of a method for hosting mobile access to dense electroencephalography data includes: receiving a set of signals, in a raw resolution, recorded by a set of channels in an electroencephalography headset during an electroencephalography test; receiving, from a client computing device, a view parameters for viewing the set of signals on a display; calculating a quantity of raw signal points per pixel column of the display based on the view parameters and a length of a segment of the electroencephalography test; for each signal in the set of signals, for each discrete contiguous sequence of the quantity of raw signal points within the segment of the signal, calculating a value set characterizing the discrete contiguous sequence of the quantity of raw signal points in the signal; and generating a static image representing value sets for each channel, in the set of channels, across the segment of the electroencephalography test.

20 Claims, 8 Drawing Sheets

METHOD FOR HOSTING MOBILE ACCESS TO HIGH-RESOLUTION ELECTROENCEPHALOGRAPHY DATA

CROSS-REFERENCE TO RELATED APPLICATIONS

This Application is a continuation of U.S. patent application Ser. No. 16/119,908, filed on 31 Aug. 2018, which claims the benefit of U.S. Provisional Application No. 62/553,021, filed on 31 Aug. 2017, each of which is incorporated in its entirety by this reference.

This Application is related to U.S. patent application Ser. No. 15/351,016, filed on 14 Nov. 2016, and U.S. patent application Ser. No. 15/831,143, filed on 4 Dec. 2017, each of which is incorporated in its entirety by this reference.

TECHNICAL FIELD

This invention relates generally to the field of electroencephalography and more specifically to a new and useful method for hosting access to high-resolution biological time series data in the field of electroencephalography.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
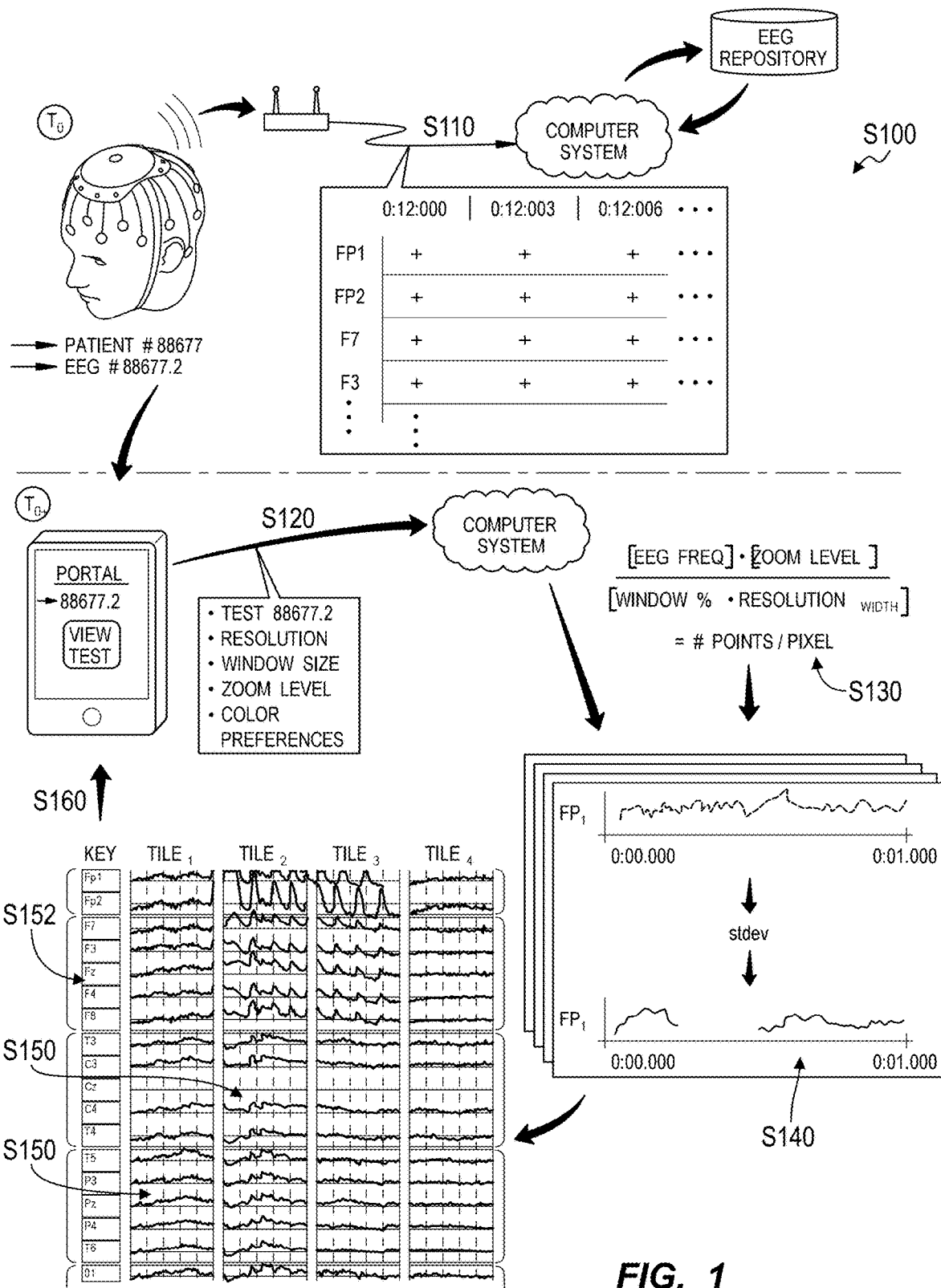
FIG. 1 is a flowchart representation of a method.

As shown in FIG. 1, a method S100 for hosting mobile access to high-resolution electroencephalography data includes, a remote computer system: receiving a first signal, in a raw resolution, recorded by a first channel in an electroencephalography headset during an electroencephalography test executed on the electroencephalography headset in Block S110; receiving, from a client computing device, a size of a viewport rendered on a display of the client computing device and a display resolution of the display in Block S120; calculating a first quantity of raw signal points in the first signal per pixel column of the display based on the display resolution, the size of the viewport, and a length of a first segment of the first signal in Block S130; for each discrete contiguous sequence of the first quantity of raw signal points within the first segment of the first signal, calculating a value set characterizing the discrete contiguous sequence of raw signal points in Block S140; generating a first static image representing value sets of discrete contiguous sequences of the first quantity of raw signal points along the first segment of the first signal in Block S150; transmitting the first static image to the client computing device, via a computer network, for rendering in Block S160; generating a second static image representing a second segment of the first signal succeeding the first segment in Block S150; and transmitting the second static image to the client computing device for rendering within the viewport in Block S160.

One variation of the method S100 includes, over a first period of time: receiving a first sequence of raw signal points recorded during an EEG test executed on an electroencephalography headset in Block S110, the first sequence of raw signal points read from a first sense channel in the electroencephalography headset during the first period of time; receiving a request to view data from the first sense channel within a viewport rendered on a display of a client computing device, a display resolution of the display, a size of the viewport from the client computing device, and a zoom level within the viewport in Block S120; calculating a first quantity of raw signal points per pixel column of the display based on the display resolution, the size of the viewport, and the zoom level in Block S130; for each discrete contiguous sequence of the first quantity of raw signal points in the first sequence of raw signal points, calculating a value set characterizing the discrete contiguous sequence of the first quantity of raw signal points in Block S140; generating a first static image representing value sets of discrete contiguous sequences of the first quantity of raw signal points along the first sequence of raw signal points in Block S150; and transmitting the first static image to the client computing device, via a computer network, for rendering within the viewport in Block S160. This variation of the method S100 also includes, over a second period of time immediately succeeding the first period of time: receiving a second sequence of raw signal points from the electroencephalography headset, the second sequence of raw signal points read from the first sense channel during the second period of time; for each discrete contiguous sequence of the first quantity of raw signal points in the second sequence of raw signal points, compressing the discrete contiguous sequence of the second quantity of raw signal points into a value set; generating a second static image representing value sets of discrete contiguous sequences of the second quantity of raw signal points along the second sequence of raw signal points; and transmitting the second static image to the client computing device for rendering within the viewport adjacent and succeeding the first static image.

Another variation of the method S100 includes: receiving a set of signals, in a raw resolution, recorded by a set of channels in an electroencephalography headset during an electroencephalography test executed on the electroencephalography headset in Block S110; receiving, from a client computing device, a size of a viewport rendered on a display of the client computing device and a display resolution of the display in Block S120; and calculating a first quantity of raw signal points per pixel column of the display based on the display resolution, the size of the viewport, and a length of a first segment of the electroencephalography test in Block S130. This variation of the method S100 also includes, for each signal in the set of signals: for each discrete contiguous sequence of the first quantity of raw signal points within the first segment of the signal, calculating a value set characterizing the discrete contiguous sequence of the first quantity of raw signal points in the signal in Block S140. This variation of the method S100 further includes: generating a first static image representing value sets for each channel, in the set of channels, across the first segment of the electroencephalography test in Block S150; and transmitting the first static image to the client computing device, via a computer network, for rendering in Block S160.

2. Applications

Generally, the method S100 can be executed by a remote computer system to: collect high-resolution time-series biosignal data recorded by an EEG headset; to store these biosignal data in a remote database; to remotely process these biosignal data into still images (e.g., "tiles") uniquely tailored to computing devices and user portals requesting access to these data; and then serve these static images to their respective user portals in (near) real-time, thereby enabling users (e.g., doctors, neurologists) to quickly access EEG test results of their subjects: on the fly; from any client computing device (e.g., a smartphone, smartwatch, tablet, or desktop computer) executing the user portal; both in real-time during EEG tests and post hoc; despite bandwidth and connectivity limitations of local computer networks; and despite processing power of the client computing device.

For example, the EEG headset may record nineteen unique sense channels at a rate of 500 Hz—or 9500 points per second—wherein each point is recorded at a resolution of 24 bits and represents an amplitude of a biosignal at the location of the corresponding sense electrode on a subject's head at the corresponding time. A 45-minute EEG test may therefore yield a digital file approaching 73 megabytes in size. Therefore, rather than load this digital file directly onto a user's client computing device or and rather than stream EEG data from the EEG headset directly to the client computing device—either of which may encounter transmission errors and delays due to local network bandwidth limitations, require power-intensive local processing at the client computing device, or require that the user be local to her subject—the remote computer system can execute Blocks of the method S100 to: leverage extensive availability of remote processing power across a computer network to aggregate and compress these high-resolution EEG test data down to smaller visual still images (or "tiles") characterized by data densities matched to current view parameters of the client computing device; and then rapidly transmit these visual images to the client computing device over a network. The user portal can then render these visual images immediately and (substantially) without further processing, thereby providing the user a sense that these EEG data are being streamed to her computing device in real-time but without requiring the user to be local to the EEG headset, without consuming a large proportion of the local network (e.g., Wi-Fi, LAN, cellular) bandwidth, and without consuming a large proportion of the computing device's processing power.

In one example, when a user requests access to view results of an EEG test of a subject via her client computing device (e.g., her tablet, smartphone, or laptop computer), such as in real-time during the EEG test or following conclusion of the EEG test, the computing device sends its current fixed and dynamic view parameters—such as display resolution, size of a viewport in which the signal data are to be viewed, a zoom level, a segment (e.g., start and stop position) of the EEG data to be viewed, and/or sense channels of interest, etc.—to the remote computer system. For each sense channel, the remote computer system can: calculate a target number of original (or "raw") sensor points in the sense channel to compress into a singular pixel (or single column of pixels) renderable on the display of the computing device based on these fixed and dynamic view parameters; and then compress each contiguous sequence of this target number of original sensor points in the sense signal into one value that can then be represented in one pixel (or one pixel column) in a static image. In particular, rather than calculate merely an average value of a contiguous sequence of the target number of original sensor points, which may obscure the presence of large signal variations within this sequence of sensor points that may be pertinent to a diagnosis or to manual identification of particular EEG features, the remote computer system can instead calculate a minimum, a maximum, an average, and a standard deviation range of this contiguous sequence of original sensor points. In this example, the remote computer system can define the standard deviation in the same units as these original sensor points such that this standard deviation value represents a degree of amplitude variation across this contiguous sequence of original sensor points, which may be particularly pertinent to detecting signals of interest and identifying these signals as a seizure, muscle movement, etc. The remote computer system can then insert a column of pixels representing this contiguous sequence of original sensor points into a static image, such as by: defining the column of pixels in a first color (e.g., black) and spanning the minimum value and the maximum value of the discrete contiguous sequence of original signal points; defining a first subset of pixels, in the column of pixels, corresponding to values between the average and a low side of the standard deviation of the discrete contiguous sequence of original raw signal points in a second color (e.g., gray); and defining a second subset of pixels, in the column of pixels, corresponding to values between the average and a high side of the standard deviation of the discrete contiguous sequence of raw signal points in the second color (shown in FIGS. 6A and 6B).

The remote computer system can: repeat this process for each contiguous sequence of original sensor points in each sense channel over a duration of the EEG test designated for one static image (e.g., 200 milliseconds); and compile these minimum, maximum, and standard deviation values into columns of pixels along sections of a new static image assigned to corresponding channels in the EEG test. The remote computer system can thus rapidly generate and send this static image to the client computing device, which can then be rendered by the client computing device in order to depict biosignal data recorded over a short duration of the EEG test (e.g., 200 milliseconds) and to visually indicate regions of interest in these original biosignal data despite current view parameters at the client computing device. The remote computer system can repeat this process to generate static images representing biosignal data over subsequent durations of the EEG test.

In particular, the remote computer system can: repeat this process for each contiguous sequence of the target number of original sensor points in each active signal recorded during the EEG test; compile these standard deviation values into one amplitude (e.g., standard deviation voltage) versus time plot per sense channel; virtually arrange these plots, such as grouped vertically by location of corresponding sense electrodes; and output a static two-dimensional color image (e.g., a frame, a tile) of these plots. The remote computer system can thus compress high-resolution, raw EEG data into a single static image exhibiting minimal loss of pertinent brain activity, wherein this single static image is of a size, geometry, and resolution matched to current view parameters at the client computing device. The remote computer system can then serve this static image to the client computing device for immediate (e.g., real-time) presentation to the user. Because this static image generated by the remote computer system is relatively small, the static image: may be served to the client computing device via a computer network relatively quickly and given less network bandwidth; and may be rendered relatively quickly by the client computing device with minimal additional processing.

Furthermore, in order to improve speed at which the remote computer system populates these plots with standard deviation values, generates static images, and sends these static images to the client computing device, the remote computer system can: segment these plots into a set of (e.g., five, ten) columnar tiles; generate a rightmost tile; serve the rightmost tile to the client computing device; generate a next-leftmost tile; serve this next-leftmost tile to the client computing device; etc. until the leftmost tile has been generated and served to the client computing device. If the user has elected to view EEG test data in real-time or playback a past EEG test at her computing device, the remote computer system can implement similar methods and techniques: to regularly generate a next tile depicting a next segment of the EEG test—such as at the playback frame rate selected at the client computing device—according to the current view parameters at the client computing device for this length of the EEG test; and to serve this next tile to the client computing device for sequential rendering (e.g., from left to right) within the viewport at the client computing device.

Figure 2:
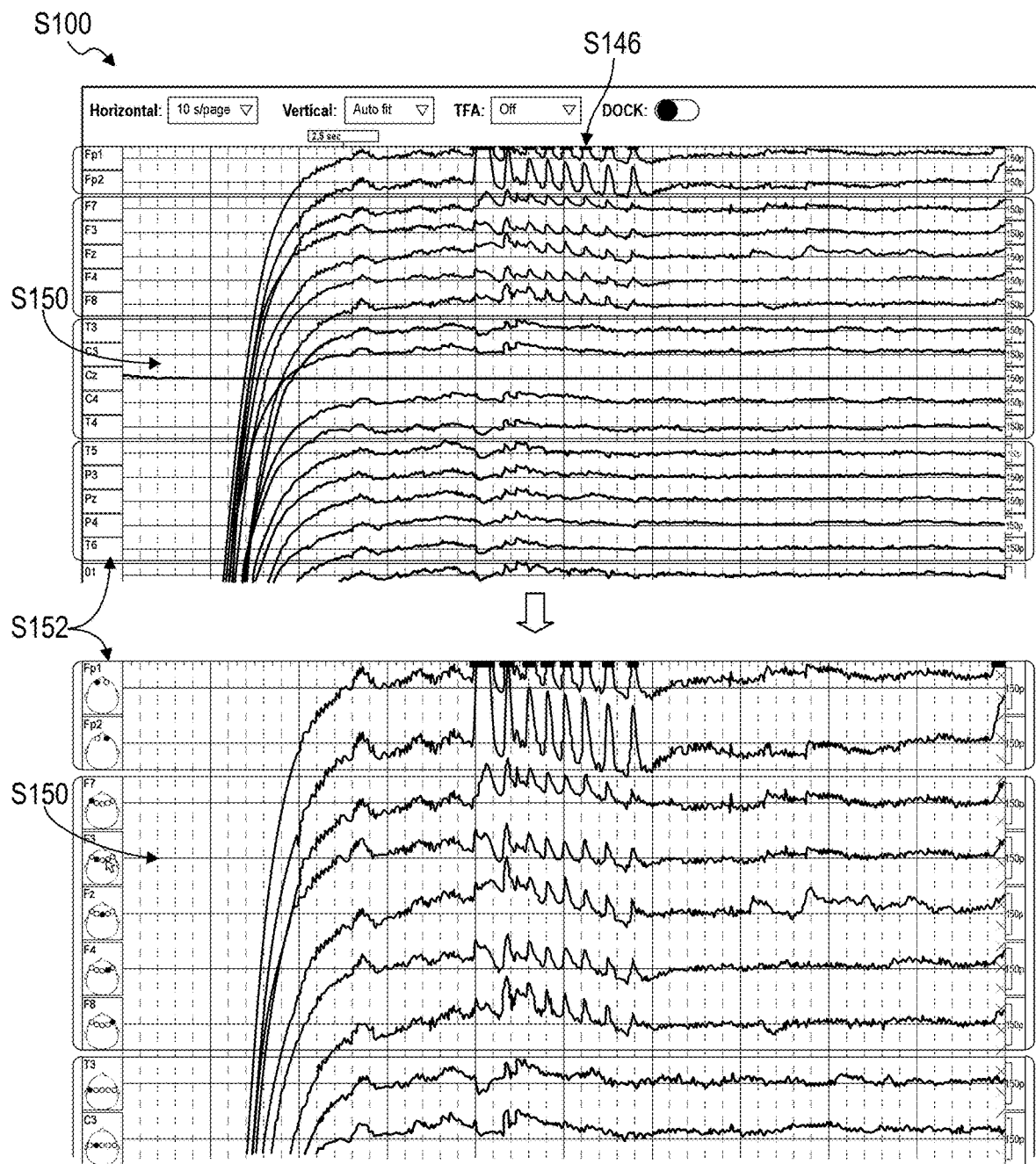
FIG. 2 is a flowchart representation of one variation of the method.

Each time the user zooms into or out of the EEG test data, activates or deactivates a sense channel, or otherwise changes view parameters for viewing these EEG test data, the remote computer system can: recalculate a target number of original sensor points per signal to compress into a singular pixel; and then repeat the foregoing processes to generate a next static image that includes compressed, low-loss representations of the EEG test data matched to these updated view parameters at the client computing device and to this target number of original sensor points per pixel (shown in FIG. 2). (The remote computer system can also pre-generate these static images or tiles in anticipation of future view parameters at the client computing device.) The remote computer system can therefore adjust compression of biosignal data from the EEG headset into static images responsive to changes in view parameters at the client computing device such that the remote computer system serves static images of relatively consistent file size to the client computing device despite a density of biosignal information represented in this static image and thus enables the user to zoom into and out of these biosignal data in real-time. (The user portal that receives these static images or tiles from the remote computer system can also cache these static images in local memory and can re-render these static images or tiles at a future time during the same viewing session if the view parameters are returned to corresponding values, thereby further limiting a total volume of data transfer between the remote computer system and the client computing device during this viewing session.)

Because the remote computer system collects and stores EEG test data in one repository, such as a remote database, the remote computer system can implement Blocks of the method S100 simultaneously to generate and serve static images for one current or past EEG test to multiple computing devices of multiple users (e.g., multiple doctors) in one or more hospitals, clinics, hospital systems, regions, or countries—local or remote to the subject—throughout the world. By compressing high-resolution EEG data into lightweight static images remotely and serving these static images to a user's client computing device for local presentation to the user rather than transferring large, complete EEG files to the client computing device—which may otherwise require an extended duration of time to download and to process locally at the client computing device—the remote computer system can also enable the user to rapidly between viewing multiple current and/or past EEG tests at her computing device with minimal lag or latency.

2.1 Distributed Processing

The method S100 is described herein as executed by a remote computer system (e.g., a remote server or a computer network) interfacing with an EEG headset to collect raw EEG test data or retrieve raw EEG data from a repository such as a database and serving compressed visual forms of these EEG test data to a user portal executing on a client computing device (e.g., a tablet, a smartphone, or other client computing device) for consumption by a user, such as a doctor (e.g., a neurologist) or an EEG test administrator. However, Blocks of the method S100 can be executed by any other local or remote computer system (e.g., locally by a client computing device, locally by an EEG headset, remotely by a remote server, etc.) to process and prepare biosignal data of any other type for rendering on a fixed or client computing device.

Therefore, high-performance remote computer systems (e.g., remote servers) can be spooled up to execute Blocks of the method S100—including aggregating, analyzing, and extracting insights from EEG data and compressing these EEG data into a series of lightweight static images (or "tiles") that can be quickly loaded onto a user's client computing device—in order to enable many client computing devices to view complex EEG data, even low-end, resource constrained client computing devices with minimal processing power. For example, the method S100 can be executed by a remote, high-performance computer system in order to: execute more resource-intensive processing and analytics of EEG data from an EEG test with minimal latency, such as signal processing (e.g., FFT), (shown in FIG. 3) artifact reduction, seizure prediction, and generation of additional visualization to represent signals recorded during the EEG test (shown in FIG. 4); and to enable portability of dense raw and processed EEG data across many client computing devices (e.g., a desktop computer with a large monitor, a laptop computer, a tablet, a smartphone, and even a smartwatch with a sub-2" screen and minimal data processing capabilities), both in (near) real-time and post hoc.

Figure 9:
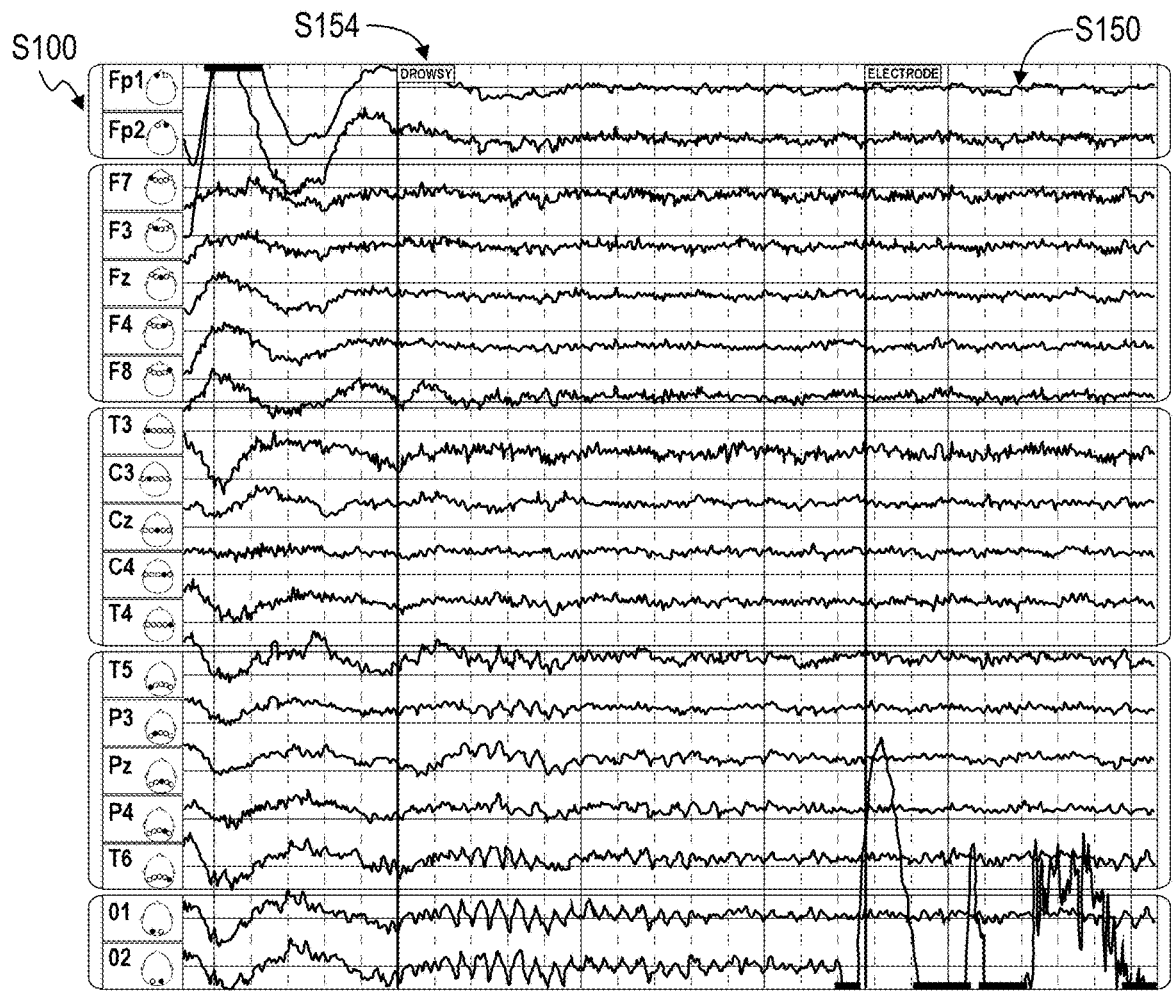
FIG. 9 is a graphical representation of one variation of the method.
Figure 10:
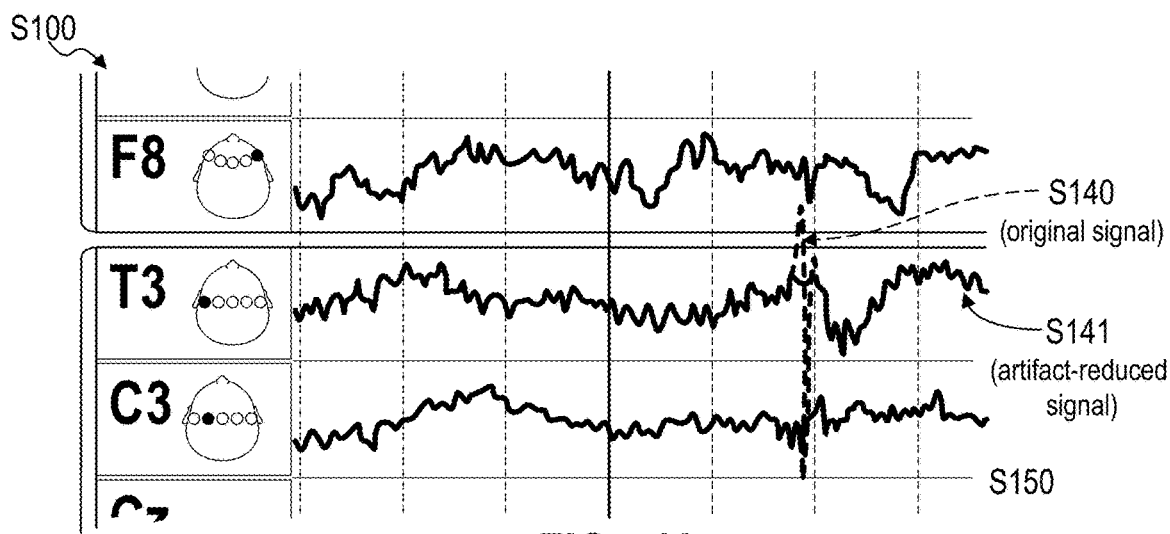
FIG. 10 is a graphical representation of one variation of the method.

Furthermore, the remote computer system can execute Blocks of the method S100 to derive more complex information from raw EEG data, such as: temporal and spatial visualizations of individual and groups of EEG signals;

minimum, maximum, and standard deviation values of segments of raw EEG data; annotations for segments of signals that represent artifacts or poor sense electrode contact quality (shown in FIGS. 7 and 8); annotations for subject and connection status (shown in FIG. 9); artifact-reduced signals (As shown in FIG. 10); etc. The remote computer system can compile these derived information and computed signals with compressed raw signals from the EEG test, annotations entered by a technician during the EEG test, a photic channel recorded during the EEG test, etc. to generate lightweight static images that represent highly-complex visual information; however, regardless of the amount of information contained in each static image and view parameters at the user's client computing device, these static images may remain (approximately) the same size (i.e., contain the same number of pixels). Therefore, a data transmission footprint for consumption of an EEG test at a client computing device according to the method S100 may be substantially fixed rather than scaling as function of an amount or type of data visualized on a client computing device.

3. EEG Headset and EEG Data

Block S110 of the method S100 recites downloading a first signal, in a raw resolution, recorded by a first channel in an electroencephalography headset during an electroencephalography test executed on the electroencephalography headset. (Block S110 can similarly recite downloading a set of signals, in a raw resolution, recorded by a set of channels in an electroencephalography headset during an electroencephalography test executed on the electroencephalography headset.) Generally, in Block S110, the remote computer system can retrieve EEG test data from an EEG headset, such as in real-time while a subject is wearing the EEG headset or upon conclusion of the EEG test.

Figure 12:
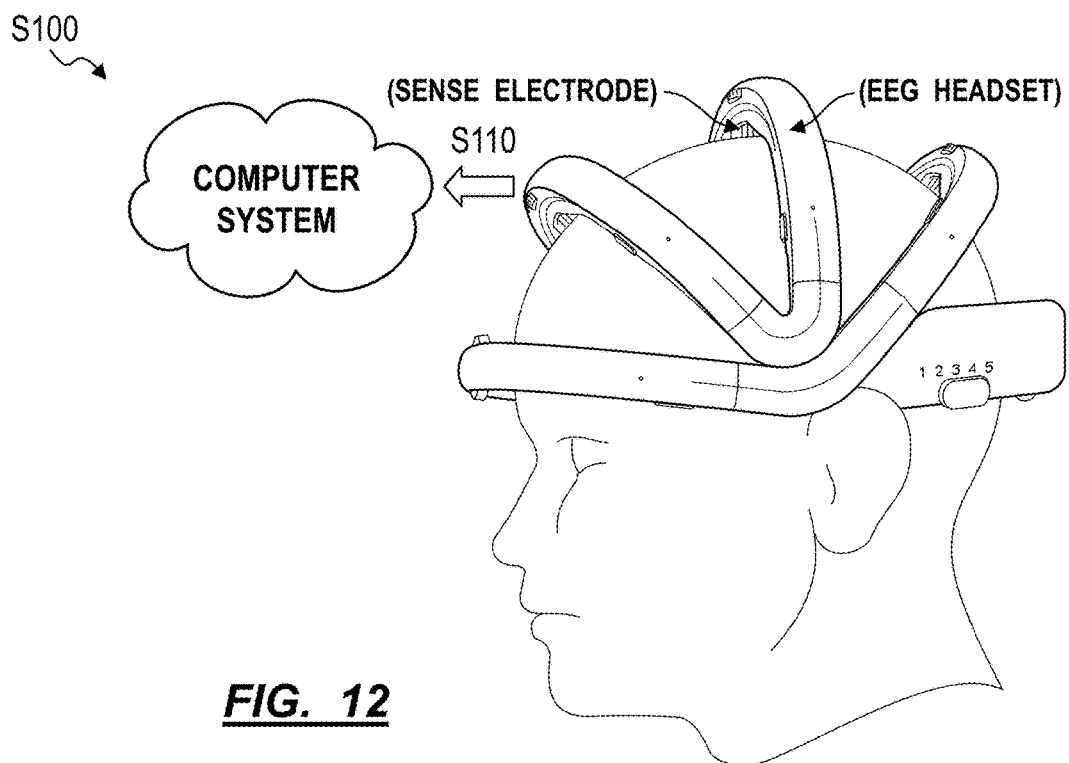
FIG. 12 is a flowchart representation of one variation of the method.

In particular, and as shown in FIG. 12, the method S100 can be executed by the remote computer system in conjunction with an EEG headset configured to collect cerebral activity (or "brain wave," "neural oscillation") data from one or more sense electrodes when the EEG headset is worn by a subject. For example, the EEG headset can include: a driven electrode configured to contact the subject's skin remote from an area of interest and to output a drive signal; a reference electrode configured to contact skin of the subject remotely from the area of interest and to detect a raw reference signal; a set of sense electrodes configured to contact the subject's skin around the area of interest and to detect sense signals from the area of interest; and a support structure configured to support and locate the driven, reference, and sense electrodes on the subject's scalp. For example, the EEG headset can include nineteen sense electrodes arranged in a 10-20 configuration spanning frontal, temporal, central, parietal, and occipital lobe regions across the subject's scalp, such as described in U.S. patent application Ser. No. 15/831,143.

The EEG headset can also include a signal processor configured: to read analog reference and sense signals from the reference and sense electrodes, respectively; to subtract the reference signal from each analog sense signal to form a set of composite analog signals; and to convert each composite analog signal into a composite digital signal, such as described in U.S. patent application Ser. No. 15/351,016. The EEG headset can also include a communication module (e.g., a wireless communication module) configured to offload these composite digital signal data to the remote computer system, such as by streaming these data to the remote computer system over a wireless network in real-time during an EEG test or transmitting a complete EEG test file to the remote computer system once the EEG test is complete. However, the EEG headset can define any other form, include any other type or combination of biometric sensors, record biometric signals from a subject in any other way, and offload these data to the remote computer system over any other wired or wireless communication protocol.

In Block S110, the remote computer system—remote from the electroencephalography headset—can: receive the raw signals streamed from the electroencephalography headset in real-time during the electroencephalography test; and then store these signals in a remote database. For example, the EEG headset can stream raw digitized signals—read from sense electrodes integrated into the EEG headset—via a local ad hoc wireless network to a local desktop computer connected to a local area network, and the local desktop computer can upload these raw digitized signals to a remote database. The remote computer system can then: access this remote database in real-time or post hoc in Block S110; and execute subsequent Blocks of the method S100 to analyze these raw digitized signals, to generate lightweight visualizations depicting these raw digitized signals and/or more complex data derived from these raw digitized signals, and to return these visualizations to a client computing device requesting access to these EEG data.

However, the remote computer system can collect or access EEG test data from the EEG headset in any other way in Block S110. The remote computer system can also access EEG test data recorded by other devices, such as by a set of loose electrodes applied to a user's skin during an EEG test.

4. Portal

Block S120 of the method S100 recites receiving—from a client computing device—a size of a viewport rendered on a display of the client computing device and a display resolution of the display. Generally, in Block S120, the remote computer system can access view parameters of a viewport at which access to EEG test data is requested, such as including: selection of a live or stored EEG test; a size (e.g., a width and height) of the viewport at the client computing device; a resolution of a display integrated into or connected to the client computing device; and a zoom level selected at the viewport. The remote computer system can store these view parameters and subsequently generate a sequence of static images depicting signals recorded during the selected EEG test according to these view parameters until the remote computer system receives a next set of different view parameters from the client computing device.

In Block S120, the remote computer system can also receive a request for live access to an electroencephalography test from the client computing device and then execute subsequent Blocks of the method S100 to generate static images depicting signals recorded during this EEG test substantially in real-time as these raw digitized signals arrive at the remote database or remote computer system from the EEG headset. Alternatively, in Block S120, the remote computer system can receive selection of a start point to begin viewing signals recorded during a selected EEG test, such as in the form of a timestamp in the EEG test selected for viewing at the viewport; the remote computer system can thus generate a sequence of static images depicting the EEG test starting at the indicated start point and according to view parameters selected and adjusted by the user at the client computing device over time.

In one implementation, the remote computer system interfaces with a user through a user portal, such as executing on a tablet, smartphone, laptop computer, or other computing device. For example, the user portal can be hosted within a native EEG review application or within a web browser executing on the client computing device. To view results of an EEG test, such as in real-time or post hoc, a user may open the user portal, enter her login credentials, and navigate to available EEG tests linked to her account, such as: EEG tests still awaiting review by the user; EEG tests ordered by the user for her past and current subjects (e.g., patients); and/or EEG tests ordered by the user and currently in process; etc. For example, the remote computer system can maintain a permissions database linking access to EEG test data to particular users via their login credentials; once the user logs in to the user portal, the user portal can query the remote computer system for EEG test data that the user is permitted to access and then populate a menu with related information (e.g., subject name and EEG test data) and links to access data recorded during these EEG tests. The user can then select one (or multiple) EEG tests to review from this menu.

Figure 3:
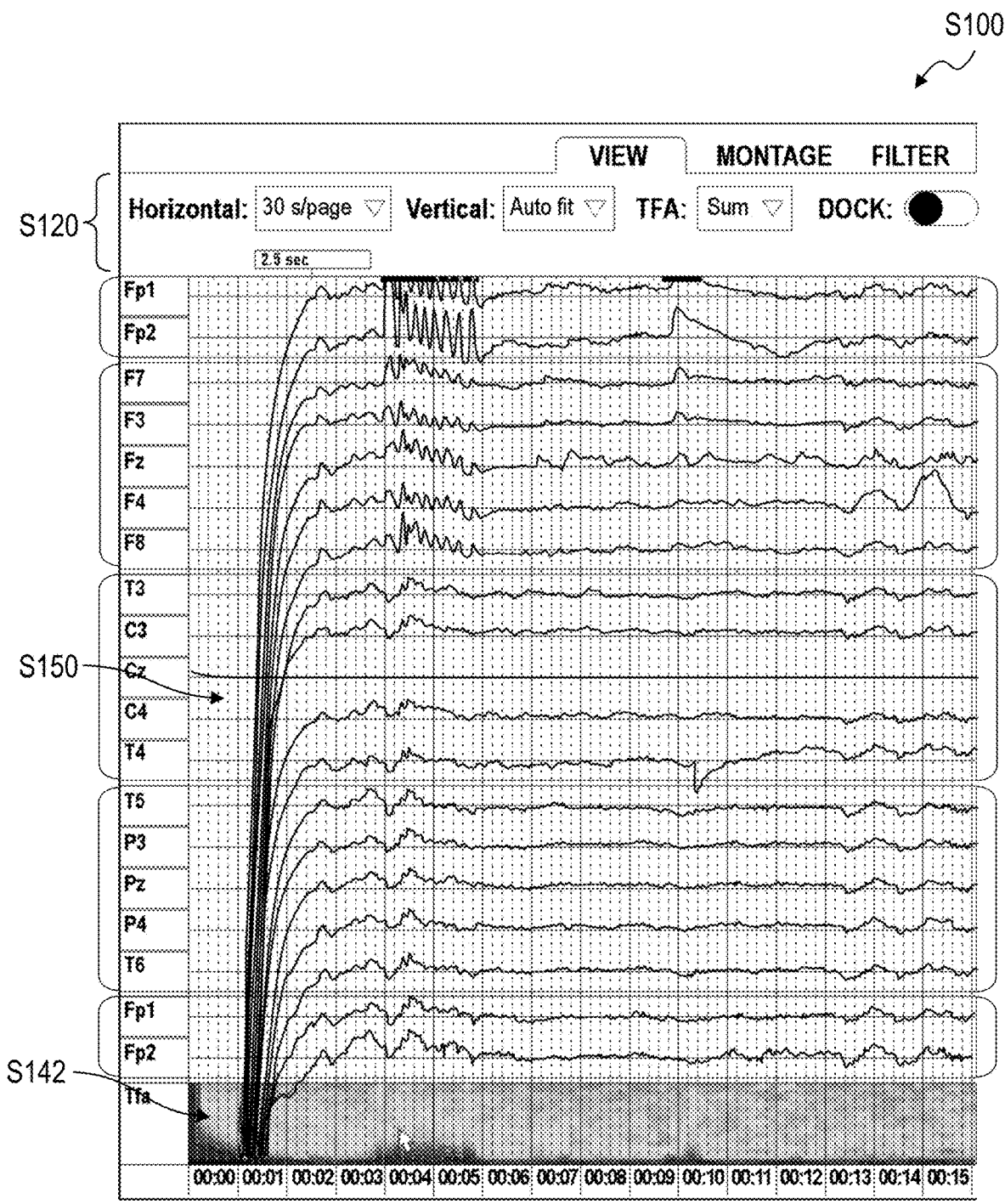
FIG. 3 is a graphical representation of one variation of the method.

Upon selection of an EEG test at the user portal, the user portal can aggregate view parameter values from the computing device, such as including: a resolution of a display integrated into or connected to the computing device; a geometry (e.g., pixel width and height) of a viewport in which sensor data from the selected EEG test is to be rendered; which sense channels are active or hidden (e.g., all nineteen 10-20 EEG sense channels set as active by default); a desired resolution (e.g., a "zoom level") for the active channels (e.g., the full width of the EEG test or a width of 30 seconds per page by default); visual attributes such as background and channel colors (e.g., green sensor points on a white background by default, or black sensor points on backgrounds color-coded by lobe location); grid line spacing (e.g., one-second primary grid lines and 200-millisecond secondary grid lines); whether time-frequency analysis (e.g., short-time Fourier transform) is active for some or all sense channels; as shown in FIG. 3. However, the user portal can aggregate any other fixed and dynamic view parameter values, such as default or last view parameter values when an EEG test is selected by the user.

Once the user portal has aggregated these view parameter values, the user portal can send a query to the remote computer system, including the view parameter values, an identifier of the EEG test selected by the user, and a request for a visual representation of data from this EEG test. Upon receipt of this query in Block S120, the remote computer system can execute subsequent Blocks of the method S100 to remotely transform data from the EEG test into a sequence or set of static images representing these EGG data according to these view parameters.

Figure 11:
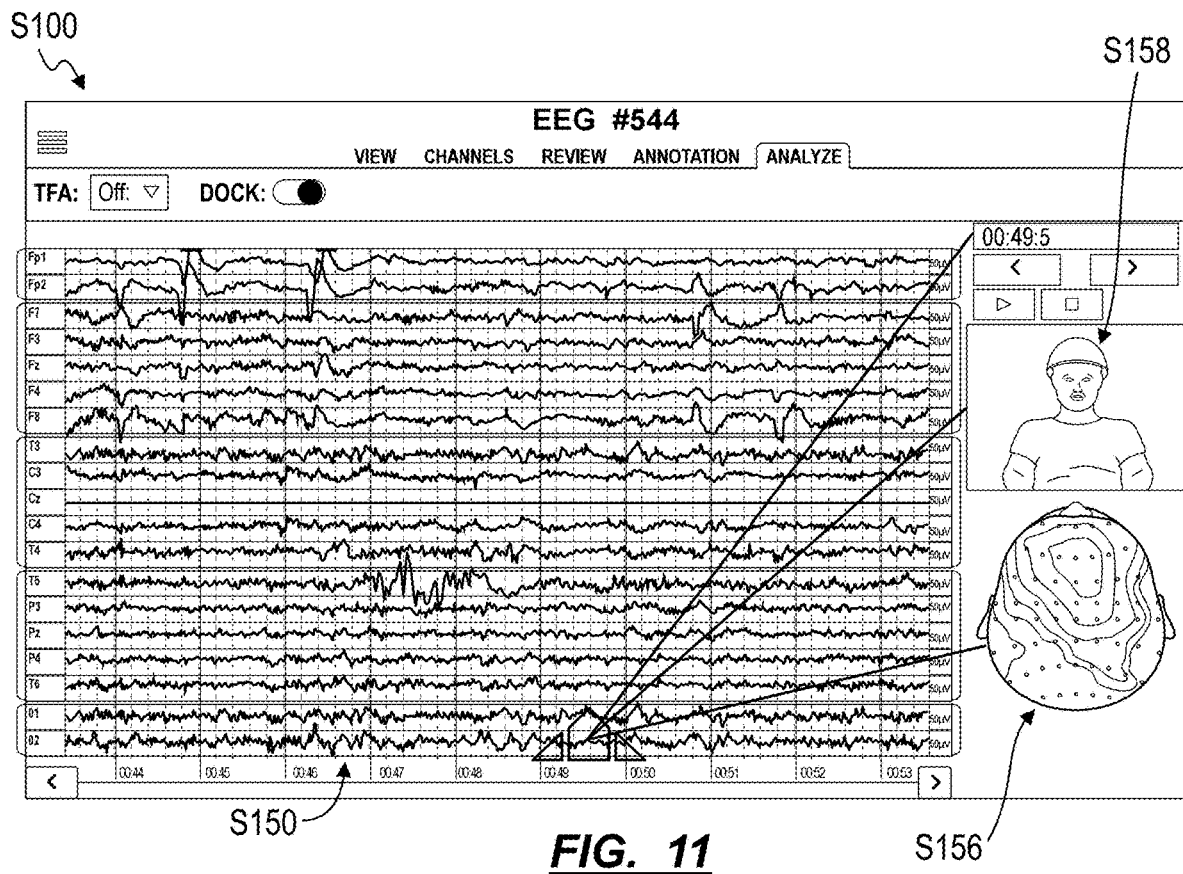
FIG. 11 is a graphical representation of one variation of the method.

The user portal can also: aggregate a set of original channels in the EEG test selected as active and as inactive at the viewport; aggregate a set of computed and secondary channels selected as active and as inactive at the viewport, such as global and channel-specific temporal heatmaps, a photic channel, a technician annotation channel, and/or artifact-reduced channels, etc.; aggregate selection of additional visualizations within the viewport, such as a video of the subject wearing the EEG headset during the EEG test or a spatial heatmap of signals recorded during the EEG test; and return these selections to the remote computer system (shown in FIG. 11). The remote computer system can then generate static images according to these additional parameters in subsequent Blocks of the method S100.

The user portal can also return an updated array of view parameters for the viewport, original and derived channel selections, and visualization selections to the remote computer system throughout playback of the EEG test at the client computing device, such as: on a regular interval (e.g., at a rate that next static images are rendered in the viewport); or selectively when a view parameter is changed at the user portal (e.g., when: a zoom level is changed, the viewport is resized, the user scrubs along the duration of EEG test, or the user activates or deactivates an original or computed channel).

However, the user portal can aggregate any other view parameters or selections and return these values to the remote computer system in any other way to inform generation of static images depicting the selected EEG test by the remote computer system.

5. Data Processing

Block S130 of the method S100 recites calculating a first quantity of raw signal points in the first signal per pixel of the display based on the display resolution, the size of the viewport, and a length of a first segment of the first signal; and Block S140 of the method S100 recites, for each discrete contiguous sequence of the first quantity of raw signal points within the first segment of the first signal, calculating a value set characterizing the discrete contiguous sequence of raw signal points. Generally, in Blocks S130 and S140, the remote computer system compresses a segment of a raw (i.e., high-resolution) original signal from the EEG test into a set of sparse EEG values: characterized by a data density matched to current view parameter values at the user portal; and that preserve regions of interest (e.g., high-amplitude-variation regions) in the channel represented in this set of sparse EEG values. In particular, the remote computer system can calculate compression parameters based on current view parameters received from the user portal in Block S130 and then implement statistic methods (e.g., standard deviation) to compress many EEG points in a raw sense signal into one quantitative value representing an amount of variation or dispersion in values per contiguous sequence of this number of raw sense signal points in each active sense channel in Block S140, thereby enabling the remote computer system to compile these singular quantitative values into a relatively small image file that can be quickly loaded onto the client computing device and rendered on its display in Blocks S150 and S160 without obscuring EEG values that may otherwise be pertinent to diagnosing the subject or detecting and identifying relevant features in these EEG data.

For example, the remote computer system can calculate a target number of raw points in the original, raw signal to collapse to a single point (e.g., a single pixel or one-pixel-wide column of pixels) renderable in the viewport at the client computing device based on current view parameters received from the remote computer system in Block S130. The remote computer system can select a next segment of the signal to depict in a next static image: starting at a last time of the EEG test depicted in the preceding static image; and spanning a period of time representing a fraction (e.g., one-fifth) of the total duration currently spanned by the viewport. The remote computer system can: subdivide this segment of the signal by discrete contiguous sequences of the target number of raw points; and calculate an average, a minimum, a maximum, and a standard deviation range for each discrete contiguous sequence of the target number of raw points in Block S140. For each discrete contiguous sequence of the target number of raw points, the remote computer system can then depict this average, a minimum, a maximum, and a standard deviation range in a column of pixels in a plot area corresponding to this channel in a next static image in Block S150 described below. The remote computer system can repeat this process of each other signal in the EEG test set as active at the viewport in Block S140 and incorporate these averages, minimums, maximums, and standard deviation range values for discrete contiguous sequence of the target number of raw points in segments of these signals corresponding to the same period of time into the same static image in Block S150 before serving this static image to the client computing device in Block S160.

Therefore, by executing Blocks S130, S140, and S150 remotely from the client computing device, the remote computer system can decouple data processing complexity and performance requirements for analyzing and depicting high-density EEG data from the client computing device.

5.1 Selective Compression Methods

In one example, the EEG headset records nineteen unique raw sense signals (corresponding to nineteen unique sense channels) at a rate of 300 Hz (i.e., 300 points per sense channel and 5700 points total per second). The client computing device (e.g., a tablet) includes a display with a resolution of 2048×1536, and the user portal currently defines a viewport spanning 70% of the width and 80% of the height of the display. From these view parameters, the remote computer system can determine that rendered EEG data can span a width of 1433 pixels. If the EEG test is exactly 30 minutes (or 1800 seconds) in length and the full width of the EEG test is to be rendered on the client computing device according to the current view parameters, the remote computer system can determine that each contiguous sequence of 378 original sensor points per raw sense signal in the EEG test data are to be compressed into a single value. Similarly, if a thirty-second segment of the EEG test data is to be rendered on the client computing device, the remote computer system can determine that each contiguous sequence of seven original sensor points per raw sense signal in the EEG test data are to be compressed into a single value. Furthermore, if a ten-second segment of the EEG test data is to be rendered on the client computing device, the remote computer system can determine that each contiguous sequence of two original sensor points per raw sense signal in the EEG test data are to be compressed into a single value. For segments of the EEG test data less than five seconds in length and rendered on the client computing device, the remote computer system can thus determine that no compression is needed, and original sensor points can instead be rendered directly.

The remote computer system can therefore selectively apply compression techniques to original sensor data. For example, the remote computer system can apply no compression techniques to original sensor data when current view parameters dictate that at least one column of pixels on the display of the client computing device is available per original sensor value in each raw sense signal (i.e., if the resolution of the display, the width of the viewport, and the zoom level in the EEG test data are all sufficiently high). In this example, the remote computer system can also calculate a linear combination (e.g., an unweighted average) of multiple original sensor values when current view parameters at the viewport dictate availability of one column of pixels on the display per two or three original sensor values in a raw sense signal.

Figure 6A:
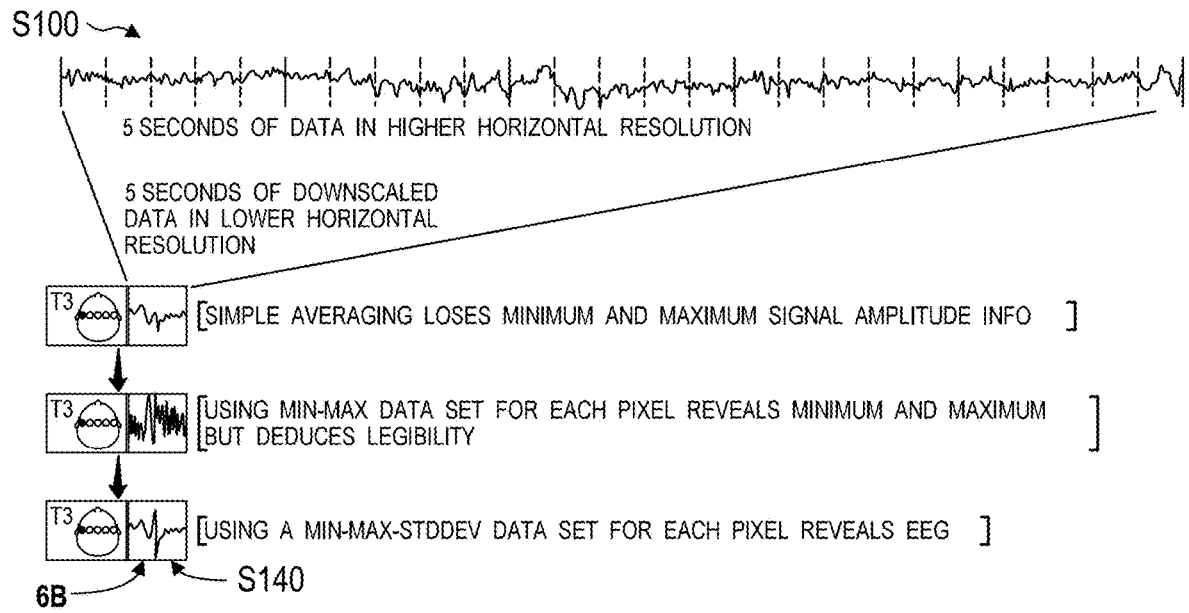
FIGS. 6A and 6B are graphical representations of one variation of the method.
Figure 6B:
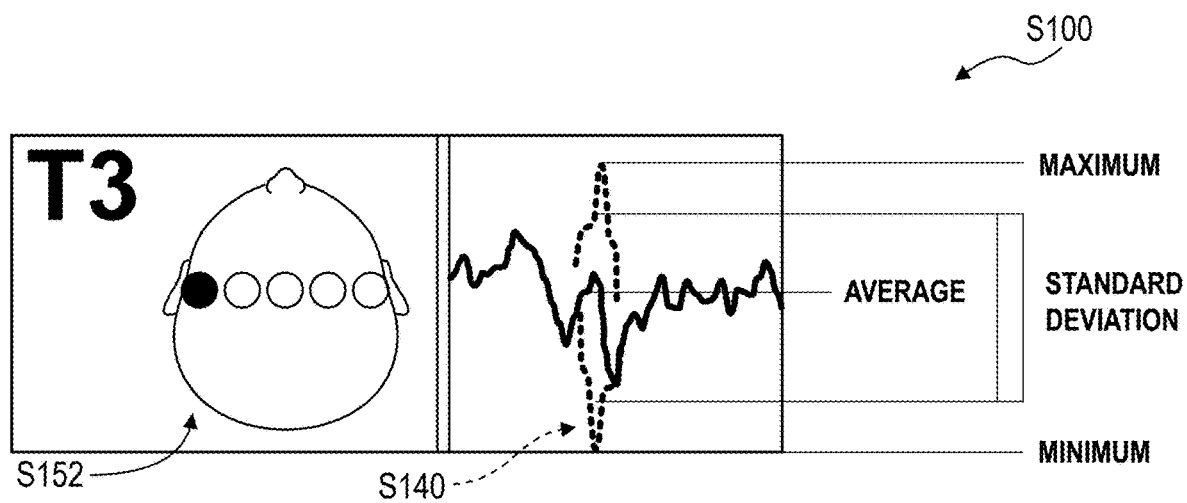

However, when current view parameters at the viewport necessitate compression of four or more original sensor values in a raw sense signal into one pixel column, the remote computer system can: extract a minimum value from a discrete contiguous sequence of (four or more) raw signal points within a signal currently set as active at the viewport; extract a maximum value from this discrete contiguous sequence of raw signal points; calculate an average of this discrete contiguous sequence of raw signal points; and calculate a standard deviation of this discrete contiguous sequence of raw signal points in Block S150. The remote computer system can then depict these values in one column of pixels in a static image in Block S150 described below, such as by: defining a column of pixels in a first color (e.g., black) and spanning the minimum value and the maximum value of this discrete contiguous sequence of raw signal points; shifting a first subset of pixels, in the column of pixels, corresponding to values between the average and a low side of the standard deviation of the discrete contiguous sequence of raw signal points from the first color (e.g., to a gray value); shifting a second subset of pixels, in the column of pixels, corresponding to values between the average and a high side of the standard deviation of the discrete contiguous sequence of raw signal points from the first color (e.g., to the gray value); and then locating this column of pixels at a location within the current static image corresponding to a time period within the electroencephalography test represented by this discrete contiguous sequence of raw signal points, as shown in FIGS. 6A and 6B. The remote computer system can execute this process for each contiguous sequence of raw signal points in a segment of this signal designated for this static image and can repeat this process for concurrent segments of each other signal in the EEG test currently set as active at the viewport.

Figure 4:
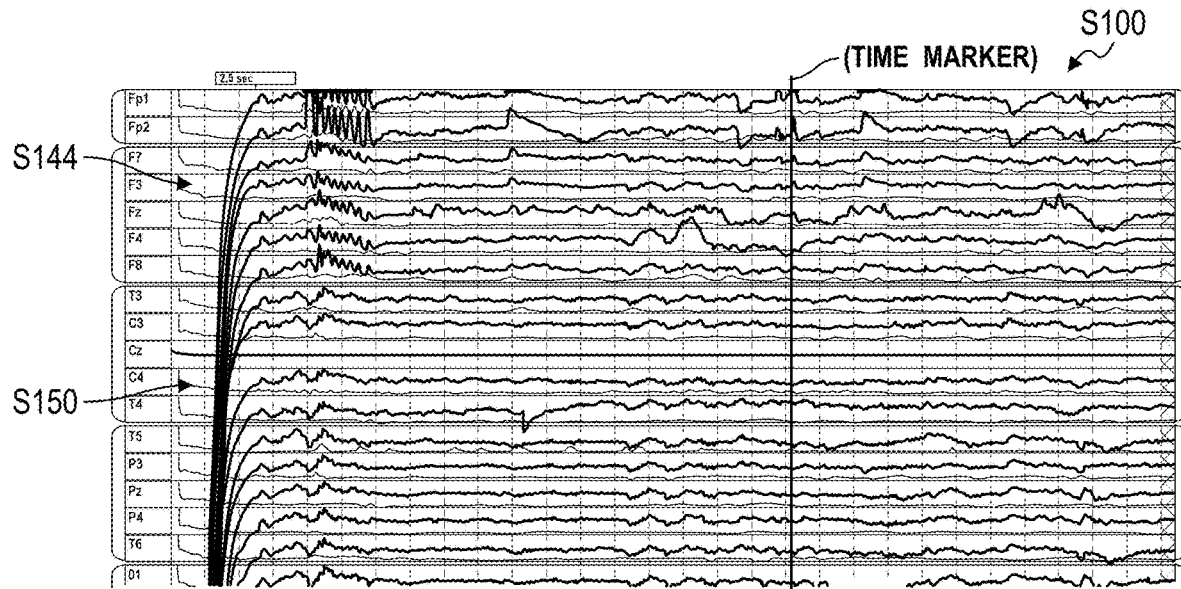
FIG. 4 is a graphical representation of one variation of the method.
Figure 5:
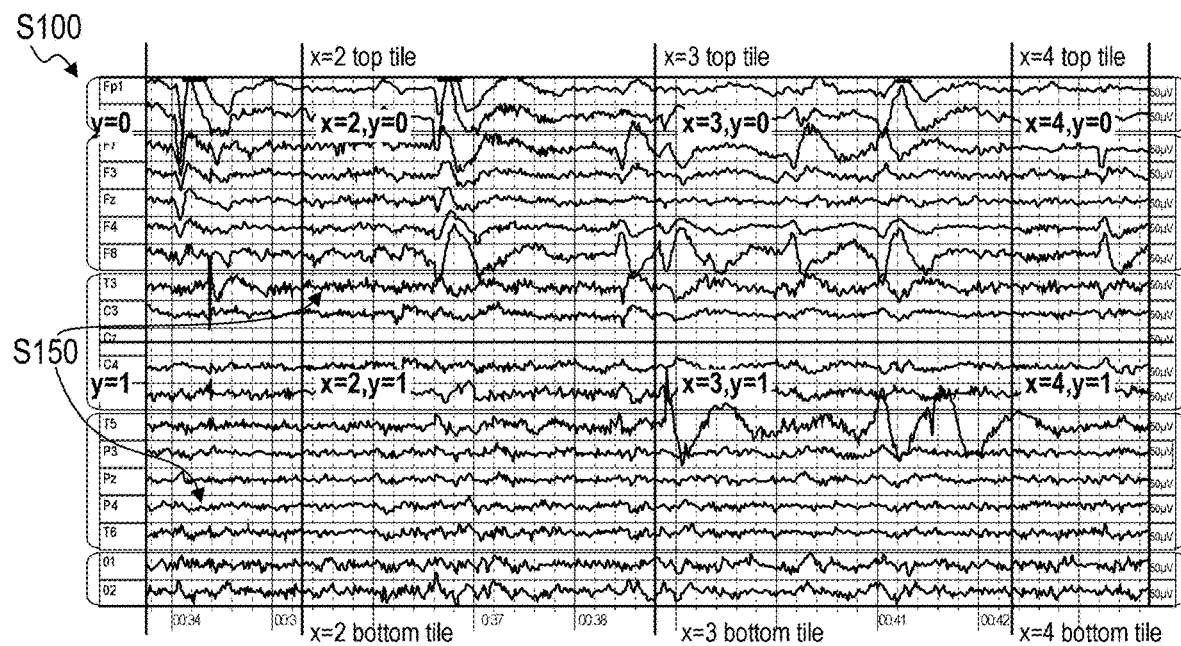
FIG. 5 is a graphical representation of one variation of the method.

Once the remote computer system calculates this quantity of raw signal points per pixel on the display of the client computing device given current view parameters received from the user portal, the remote computer system can: segment each raw sense signal (currently set as active at the user portal) from the EEG test into discrete, contiguous segments of original sensor values, such as shown in FIG. 5; compress each discrete, contiguous segment of original sensor values into one quantitative value or a quantitative value set according to a statistical method assigned to this degree of compression, such as shown in FIG. 6B; and temporally align these quantitative values per sense channel to generate a set of (e.g., nineteen) compressed sense signals, each containing one point per pixel column across a fraction of the viewport rendered on the client computing device (e.g., 100% of the width of the viewport for post hoc viewing of the EEG test, or one-fifth of the width of the viewport for real-time viewing of the EEG test), as shown in FIG. 2. In particular, the remote computer system can aggregate quantitative value sets representing a sense signal into a virtual line plot with time on an x-axis and amplitude on a y-axis within a section of a next static image designated for this sense channel, as shown in FIGS. 1, 2, 3, and 4.

5.2 Selective Channel Compression

The remote computer system can implement the foregoing processes to "compress" the full duration of all raw sense signals in the EEG test data (or the remainder of each raw sense signal in the EEG test selected for viewing at the client computing device) according to the current view parameters.

Alternatively, the remote computer system can selectively implement the foregoing processes to "compress" concurrent discrete segments of raw sense signals in the EEG test into a discrete static image—spanning a division of time spanned by the viewport—at a rate substantially similar to a frame rate at which the client computing device updates and renders a next static image in the viewport. In particular, the remote computer system can sequentially compress segments of raw sense signals in the EEG test into discrete static images and "drip feed" these static images to the client computing device.

The remote computer system can also implement the foregoing methods and techniques to compress only raw sense signals of sense channels currently set as active at the viewport. Furthermore, the remote computer system can implement this process asynchronously when the user has elected to view a past EEG test or in real-time responsive to inbound EEG test data when the user has elected to view this EEG test that is currently in-process.

6. Computed and Secondary Channels

In variations shown in FIGS. 3, 4, 7, 8, 9, 10, and 11, the remote computer system computes additional signals from original, raw signals recorded during the EEG test.

6.1 Global TFA

In one variation shown in FIG. 3, the remote computer system aggregates multiple raw sense signals from the EEG test into a composite signal—in a time domain—and converts this composite signal into a frequency domain (e.g., by implementing Fourier transform techniques) in Block S142, which may reveal dominant brain frequencies presenting in the subject during the EEG test.

For example, once the remote computer system has segmented each raw sense signal in the EEG test into multiple discrete, contiguous segments of original sensor values based on the current zoom level, viewport width, and resolution of the display of the client computing device, the remote computer system can: aggregate one such segment of original sensor values from all sense channels occurring over the same period of time into one composite sense signal; and then implement time-frequency analysis techniques (e.g., a short-time Fourier transform) to extract frequency domain information from the composite sense signal. The remote computer system can then compress these frequency domain information based on current view parameters at the viewport, such as according to methods and techniques described above.

The remote computer system can then incorporate this frequency domain information as an additional channel represented in the static image generated in Block S150 and time-synchronized to other sense channels represented in this static image, such as shown in FIG. 3. In one example, the remote computer system can represent this compressed composite signal in a virtual heatmap with time—synchronized to other channels in the EEG test—on an x-axis, frequency (e.g., from 0 Hz to 30 Hz) on a y-axis, and color as a function of amplitude of the composite sense signal (e.g., dark blue for zero amplitude; dark red for high-amplitude). However, the remote computer system can depict spectral distribution of all (or a selected subset of all) signals in the EEG test with a heatmap of any other form.

Therefore, in one example, the remote computer system can receive a set of signals, in a raw resolution, recorded by a set of sense electrodes in the electroencephalography headset during the electroencephalography test in Block S110. For each signal in the set of signals, the remote computer system can: select a segment of the signal spanning a duration of time during the electroencephalography test queued for rendering within the viewport; and, for each discrete contiguous sequence of the first quantity of raw signal points within the segment of the signal, calculate a value set characterizing the discrete contiguous sequence of raw signal points in Block S130. The remote computer system can then: aggregate the set of signals into a composite signal; and calculate a temporal heatmap of amplitudes of a range of frequencies within the composite signal. Subsequently, in Block S150, the remote computer system can: for each signal in the set of signals, represent value sets of discrete contiguous sequences of the first quantity of raw signal points along the segment of the signal within a horizontal section of the first static image corresponding to a sense electrode, in the set of sense electrodes, that recorded the signal during the electroencephalography test; and represent a segment of the temporal heatmap corresponding to the duration of time in a horizontal section of the first static image assigned to the composite signal and vertically aligned with horizontal sections of the first static image corresponding to the set of sense electrodes.

The remote computer system can implement similar methods and techniques to extract frequency domain information from groups of raw sense signals, such as from signals recorded by all occipital lobe sense channels in the EEG headset.

6.2 Channel TFA

In one variation shown in FIG. 4, the remote computer system similarly: implements time-frequency analysis techniques to extract frequency domain information from an individual raw sense signal: compresses frequency domain information for this channel based on current view parameters at the viewport, such as described above in Block S144; incorporates this frequency domain information into a section of the next static image associated with this channel (e.g., below or overlayed over a time amplitude plot representing the same signal) in Block S150. For example, the remote computer system can insert a time-frequency plot of a particular channel behind the compressed time-amplitude plot for the particular channel when generating the next static image in Block S150, as shown in FIG. 4.

6.3 Head Movement and Artifacts

In another implementation, the EEG headset can record its motion during the EEG test, such as in the form of a time series of accelerations recorded by an accelerometer integrated into the EEG headset. The remote computer system can then leverage motion data recorded by the EEG headset during the EEG test to isolate segments of the EEG test that are distorted due to motion artifacts.

Generally, quick head movements by a subject during the EEG test may yield muscle artifacts, which do not constitute cerebral activity but which may produce unexpected waveforms superimposed over cerebral activity recorded by sense electrodes in the EEG headset during the EEG test. Therefore, the remote computer system can generate a motion channel—such as including a time series of total acceleration amplitude along pitch and roll axes of the EEG headset—based on motion data recorded by the EEG headset during the EEG test. By incorporating this motion channel—synchronized to sense signals recorded during the EEG test—into static images depicting the EEG test, the remote computer system can provide a user (re)viewing the EEG test with a visual indicator of segments of these EEG signals recorded during periods of significant head movement.

6.4 Artifacts and Signal Quality

Figure 8:
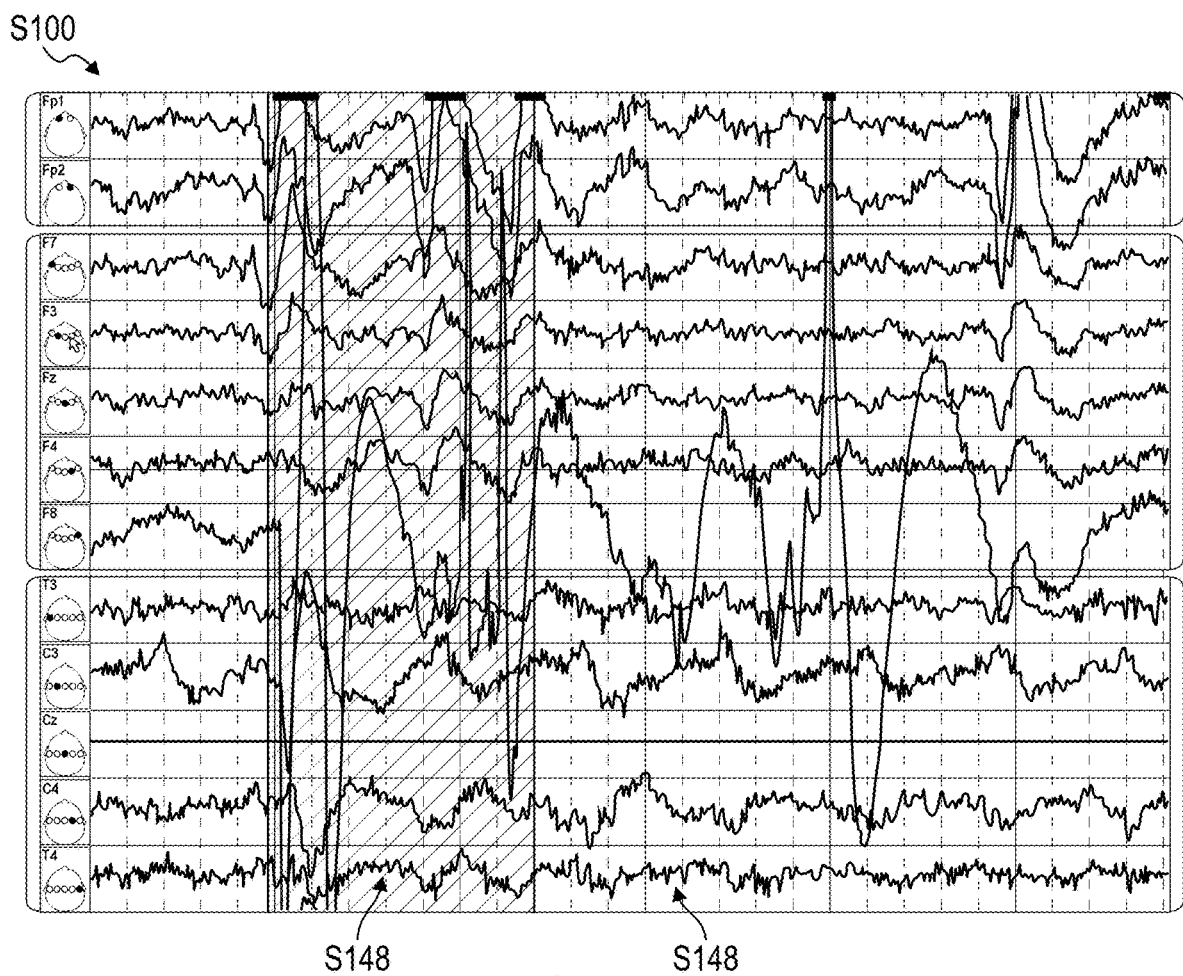
FIG. 8 is a graphical representation of one variation of the method.

In another implementation, the remote computer system can: isolate a segment of a sense signal containing artifacts that substantially overwhelm cerebral activity present in the subject and can flag this segment of this sense signal; remove or highlight this segment from the sense signal (e.g., drive a waveform in this segment of the sense signal to null, or overlay a translucent mask over this segment of this sense signal), as shown in FIG. 8; and/or generate an artifact-reduced signal that excludes this segment of the original sense signal in Block S141, as shown in FIG. 10. In particular, EEG data may be prone to various artifacts that inhibit interpretation of these data, such as: artifacts of biological origin (e.g., muscle movement); known and expected artifacts (e.g., eye blinks); and artifacts resulting from electrical phenomenon (e.g., main electrical power interference). The remote computer system can therefore identify and selectively handle segments of a signal exhibiting such artifacts.

In one example, the remote computer system scans a segment of a signal for a subsegment representing an artifact before compressing and representing this segment of the signal in a next static image. In this example, the remote computer system can implement a deep learning model to determine whether this segment of the signal includes a substantive artifact and can confirm a detected artifact responsive to a concurrent motion signal in the motion channel described above exceeding a threshold amplitude. The remote computer system can also generate a processed waveform representing this segment of the first signal; responsive to detecting (and confirming) an artifact in a subsegment of this signal, the remote computer system can attenuate this subsegment in the processed waveform. The remote computer system can then: execute the forgoing methods and techniques to compress both the segment of the original signal and the corresponding segment of the processed waveform into a series of value sets in Block S140; represent the value set of each discrete contiguous sequence of raw signal points along this segment of the original signal with pixels in a first color set (e.g., gray or grayscale) over a first section of a background image associated with this channel; and similarly represent the value set of each discrete contiguous sequence of points along this segment of the processed waveform with pixels in a second color set (e.g., black) over the same section of the background image associated with this channel in Block S150.

The remote computer system can thus depict both the segment of the original signal and the artifact-reduced waveform of this segment of the sense channel concurrently in one static image, thereby enabling a user to view both: this signal with artifacts-ridden segments suppressed, which may be easier for the user to interpret; and a compressed form of the original signal, which may include more complete information.

6.5 Contact Quality

Figure 7:
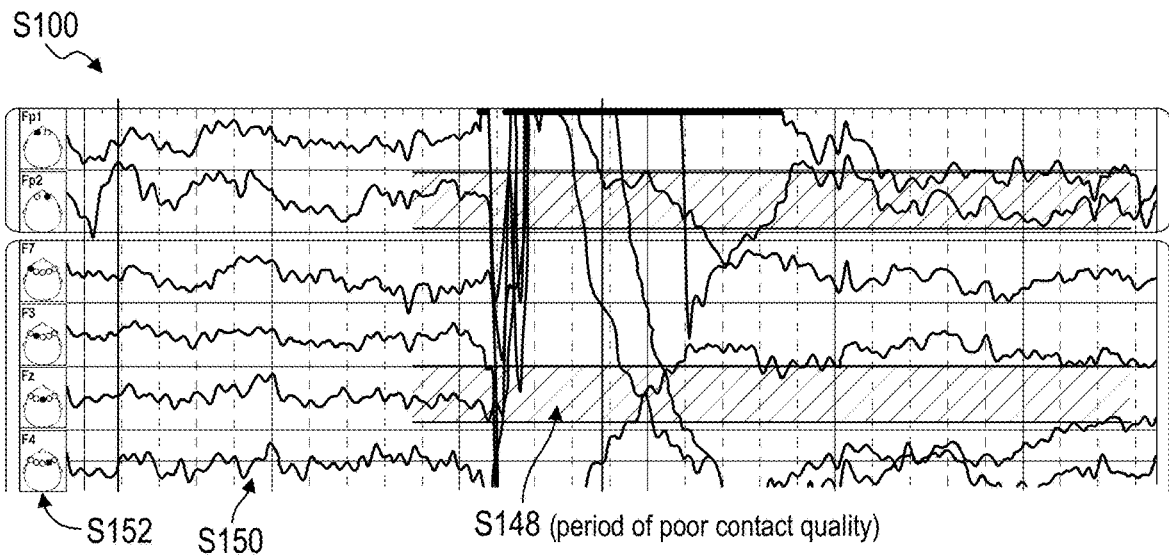
FIG. 7 is a graphical representation of one variation of the method.

In another implementation, the EEG headset (or the remote computer system) can qualify contact quality with the subject's scalp for each sense electrode in the EEG headset throughout the duration of the EEG test, such as described in U.S. patent application Ser. No. 15/351,016. For each sense signal in the EEG test, the remote computer system can thus generate a secondary contact quality channel depicting contact quality of the sense signal in Block S148 and then incorporate a segment of this secondary contact quality channel adjacent (e.g., below, overlayed over) a concurrent segment of the original signal in a static image in Block S150, as described below. In this implementation, the remote computer system can implement methods and techniques similar to those described above to suppress a subsegment of a signal over which poor contact between the subject's scalp and the corresponding sense electrode is detected, as shown in FIG. 7. Alternatively, in this implementation, the remote computer system can: represent value sets calculated from contiguous sequences of raw signal points in the signal corresponding to periods of sufficient contact quality at the corresponding sense electrode in a first color set (e.g., black; grayscale) in a static image; and represent value sets calculated from contiguous sequences of raw signal points in the signal corresponding to periods of insufficient (i.e., "poor") contact quality at the sense electrode in a second color set (e.g., red) in the static image in order to indicate detection of poor contact quality. (The remote computer system can similarly represent value sets calculated from contiguous sequences of raw signal points in the signal corresponding to periods in which substantive artifacts or other noise were detected in a third color set (e.g., yellow) in this static image.)

6.6 Photic Frequency

In another implementation, the EEG headset (or a second synchronized computing device nearby) records timestamps of photic triggers during the EEG test—that is, times at which a strobe light near the subject is activated during the EEG test. In this implementation, the remote computer system can generate a photic trigger channel depicting these instances and synchronized to sense channels in the EEG test. The remote computer system can then represent this photic trigger channel in a static image in Block S150. More specifically, the remote computer system can: receive a time series of photic flashes output by a strobe proximal the patient during the electroencephalography test in Block S110; and then represent this time series of photic flashes in a horizontal section of a static image assigned to a photic channel and vertically aligned with (i.e., temporally synchronized with) horizontal sections of the static image depicting sense signals in Block S150.

6.7 Technician Annotations

Throughout the EEG test, a technician may manually enter annotations related to the EEG test and/or to the subject, and these annotations can be timestamped and stored with EEG test data. For example, the remote computer system can execute the method S100 in real-time during the EEG test and serve static images depicting EEG data collected during the EEG test to the technician's client computing device (e.g., a tablet, a smartphone) with minimal latency (e.g., less than one second from recordation) for immediate rendering within a viewport on the technician's client computing device. The remote computer system can then interface with the client computing device, as described below, to record and timestamp annotations entered by the technician, such as in the form of textual notes entered manually or icons selected from a dropdown menu within the viewport. The remote computer system can then generate a technician annotation channel containing these annotations and incorporate this technician annotation channel into a next set of static images generated by the remote computer system when the EEG test data is viewed again at a later time, such as by inserting segments of this technician annotation channel below synchronized segments of compressed sense signals from the EEG test.

Alternatively, the remote computer system can insert a technician annotation tag over a section of a static image depicting a sense signal rather than depict this annotation in a separate technician annotation channel. For example, the remote computer system can: download a time series of annotations input by a technician viewing a patient wearing the electroencephalography headset during the electroencephalography test in Block S110; and then populate a static image with a technician flag containing a textual annotation extracted from a segment of the time series of annotations corresponding to a duration of time of sense signal segments depicted in the static image and temporally aligned to these sense signal segments in Block S154, as shown in FIG. 9.

6.8 Heartrate

In another implementation, the EEG headset includes a heart rate monitor configured to detect the subject's heart rate during the EEG test. In this implementation, the remote computer system can access a time series of the subject's heartbeats during the EEG test in Block S110, generate a heart rate channel depicting this time series of heartbeats, and incorporate segments of this time series—synchronized with sense signal data—into static images generated in Block S150 described below.

7. Static Image Generation

Block S150 of the method S100 recites generating a first static image representing value sets of discrete contiguous sequences of the first quantity of raw signal points along the first segment of the first signal. Generally, in Block S150, the remote computer system generates a static image defining a two-dimensional visual representation of results of the selected EEG test and matched in size and resolution, etc. to current view parameters at the user portal.

7.1 Background Image

In one implementation, the remote computer system retrieves a static background image and then compresses and skews this static background image for the viewport size, geometry, and resolution in the user portal and a vertical scroll position of the EEG test results within the user portal. For example, the static background image can define twenty colored rectangular regions (e.g., one per nineteen sense channels and one composite sense channel) representing sense channel plots and grouped by color.

The background image can also include: major time grid lines (e.g., on one-second intervals); minor time grid lines (e.g., on 200-millisecond intervals); and/or channel amplitude range markers for each sense channel plot. Alternatively, the remote computer system can separately populate the static background image with major and minor time and amplitude grid lines according to the current zoom level and size of the viewport.

7.2 Data Aggregation

Once the static background image is thus prepared, the remote computer system can: aggregate compressed sense signals generated in Block S140 for a time period in the EEG test queued for presentation on the user's client computing device; and then overlay these compressed sense signals onto corresponding rectangular regions in the background image to generate a static image for the period of the EEG test in Block S150.

In one implementation, the background image includes rectangular regions for additional computed and secondary channels; and the remote computer system selectively removes rectangular regions allocated for computed and secondary channels currently disabled by the user at the client computing device. For computed and secondary channels—such as described above—currently set as active, the remote computer system can overlay compressed variants of segments of these computed and secondary channels onto corresponding rectangular regions in the background image when a generating static image for a period of the EEG test in Block S150. For example, the remote computer system can: overlay a segment of a global TFA signal over a global TFA region of the background image; overlay a segment of a technical annotation channel over a technician annotation region of the background image; overlay a segment of heart rate signal over a heart rate region of the background image; and overlay both a compressed original sense signal in a first color set (e.g., redscale) and a compressed artifact-reduced sense signal in a second color set (e.g., grayscale) over a corresponding sense signal region of the background image for each active sense channel in the EEG test.

The remote computer system can thus compile the static background image and compressed sense signal points projected onto the static background image into a single static image and then transmit this static image to the client computing device for immediate rendering within the user portal in Block S160, as shown in FIGS. 2-4.

Alternatively, in one variation the remote computer system can generate an image mask or overlay containing (black or colored) pixels representing compressed sensor signals for all active channels but that is otherwise transparent. The remote computer system can return this static image mask to the client computing device, and the user portal can: retrieve the static background image, such as from local memory or a remote database; transform the static background image to fit within a viewport rendered on the display; overlay the static image mask over the static background image locally at the computing device; and then render this composite image on the display of the computing device.

7.4 Key Image

In one variation shown in FIGS. 1 and 2, the remote computer system also generates a key image renderable on the display of the client computing device adjacent the viewport and that contains persistent information for signals depicted in static images rendered within the viewport in Block S152.

In one implementation, the remote computer system accesses a key image including a column of icons ordered according to a standard columnar order in which EEG channels are displayed. In this implementation, each icon in the key image can depict a location of a sense electrode—on the EEG headset—that recorded a signal depicted in a horizontally-adjacent region of a static image concurrently rendered in the user portal. For example, each icon can include: a graphical depiction of a plan view of a subject's head; a symbol (e.g., a "dot") overlayed on this graphical depiction at approximately a plan-view location of the corresponding sense electrode; a channel name or channel identifier of the corresponding sense electrode; and/or a background color corresponding to a sense electrode group associated with the corresponding sense electrode, as shown in FIG. 2. The key image can also include icons and channel names horizontally-aligned with static image regions allocated for computed and secondary channels.

The remote computer system (or the client computing device) can also scale the key image based on the size of the viewport in order to align each icon in the key image with the section of an adjacent static image—rendered in the viewport—containing a segment of a sense signal recorded by the corresponding sense electrode. Upon receipt of the key image, the client computing device can render the key image immediately to the right of the viewport, such as before initiating playback of static images depicting segments of the EEG test.

In this implementation, the remote computer system can also overlay status information for each channel over or adjacent the corresponding icon in the key image. For example, the remote computer system can highlight an icon or the sense electrode symbol on this icon in a first color (e.g., green) responsive to determining that the corresponding sense electrode has maintained sufficient contact quality throughout a segment of the EEG test depicted in a next static image generated by the remote computer system; however, the remote computer system can highlight an icon or the sense electrode symbol on this icon in a second color (e.g., red) responsive to determining that the corresponding sense electrode has exhibited poor contact quality throughout a segment of the EEG test depicted in a next static image generated by the remote computer system. In another example, the remote computer system can highlight an icon in the key image in a first color (e.g., green) while the corresponding channel (e.g., a sense, computed, or secondary channel) is set as active at the viewport; however, the remote computer system can highlight an icon in the key image in a second color (e.g., red) responsive to the user muting the corresponding channel at the viewport. Alternatively, responsive to the user muting a channel at the viewport, the remote computer system can crop the corresponding icon out of the key image and remove the corresponding region—allocated for this channel—from subsequent static images generated by the remote computer system in Block S150; and vice versa.

In this example, the remote computer system can implement the foregoing processes to update the key image response to a change in the state of each sense, computed, and secondary channel in the EEG test. The remote computer system can then serve an updated key image to the client computing device for immediate rendering adjacent the viewport responsive to such a change in the state of a channel. Alternatively, the remote computer system can generate and transmit one persistent key image, as described above, to the client computing device; the client computing device can render (and rescale) this persistent key image adjacent the viewport throughout playback of the EEG test; the remote computer system can implement methods and techniques described above to generate a key image mask depicting states of sense, computed, and secondary channels and aligned with corresponding channel regions in the persistent key image and serve a new key image mask to the client computing device responsive to a channel state change; and the client computing device can overlay this key image mask over the persistent key image upon receipt from the remote computer system.

However, the remote computer system can generate a key image (or key image mask) renderable adjacent (e.g., rightward of) the viewport during playback of static images depicting the EGG test at the client computing device.

7.3 Clipping

In one variation, the remote computer system also detects a segment of a compressed sense signal that falls outside the bounds of the static background image and represent this segment of the compressed sense signal as an emboldened line along a corresponding segment of the perimeter of the static background image in Block S146, thereby visually indicating that this segment of the compressed sense signal has been clipped, as shown in FIG. 2.

8. Static Image Transmission, Size, and Queue

Block S160 recites transmitting the first static image to the client computing device, via a computer network, for rendering. Generally, in Block S160, the remote computer system can transmit this static image to the client computing device—such as via a cellular network, the Internet, or via a local network—for (substantially) immediate rendering.

8.1 Full-Span Static Images and Post Hoc Playback

In the foregoing implementations, the remote computer system can generate a static image (or image mask or overlay) that spans the full width and height of the viewport rendered within the user portal, such as for post hoc viewing of an EEG test.

For example, the remote computer system can receive sense signals, in the raw resolution, recorded by the electroencephalography headset over a first period of time via a computer network. When a user at a client computing device later requests access to this EEG test, the remote computer system can receive—from this client computing device at a second time succeeding the first period of time—a width dimension of the viewport rendered on the display, the display resolution of the display, a zoom level selected at the viewport, and a first timestamp in the electroencephalography test selected for viewing at the viewport in Block S120.

The remote computer system can then: transform the width dimension of the viewport and the zoom level into a duration of time encompassed by the viewport at the second time; and, for each sense signal indicated as active at the viewport, select a segment of the signal spanning this duration of time and including the first timestamp in the electroencephalography test. The remote computer system can then compress these segments of these active sense signals in Block S140 and overlay these compressed sense signal segments over corresponding regions of a background image—adjusted to span the width of the viewport—to complete a static image for the current segment of the EEG test requested at the client computing device. The remote computer system can immediately transmit the first static image to the client computing device (i.e., at approximately the second time).

The remote computer system can then immediately repeat this process: to generate a next static image representing sense signal segments during a period of time immediately succeeding the period of time represented by the last static image and representing the same duration of time as the last static image (unless the remote computer system receives a view parameter change from the client computing device) in Block S150; and to transmit this next image to the client computing device in Block S160, thereby enabling the client computing device to continuously playback the EEG test from a default start point at the beginning of the EEG test or from the initial start point selected by the user at the client computing device.

In this implementation, the client computing device can replace a last static image with a next static image received from the remote computer system on a regular interval. Alternatively, the client computing device can wipe a next static image into the viewport from a left side of the viewport while wiping a previous static image out of the viewport toward a right side of the viewport, thereby rendering a continuous, sweeping depiction of the EEG test within the viewport.

8.2 Tiles and Real-Time Playback

Alternatively, the remote computer system can generate a set of tiles that span sub-widths (and sub-heights) of the viewport, as shown in FIG. 1. For example, the remote computer system can implement the foregoing methods and techniques to generate a first static tile (or tile mask or overlay) spanning the full height and one-tenth of the width of the viewport and representing compressed sense signals over one-tenth of the duration of time represented across the width of the viewport. Upon receipt of this first static tile, the user portal can render the first static tile in a left-most position in the viewport. The remote computer system can then similarly generate a second static tile spanning the full height and one-tenth of the width of the viewport and representing compressed sense signals over a next period of time of the same duration represented by the first static tile. Upon receipt of this second static tile, the user portal can move the first static tile one tile width to the right and render the second static tile in the left-most position in the viewport. The remote computer system can then generate a third static tile spanning the full height and one-tenth of the width of the viewport and representing compressed sense signals over a next period of time of the same duration represented by the first and second static tiles. Upon receipt of this third static tile, the user portal can move the first and second static tile one tile width to the right and render the third static tile in the left-most position in the viewport. The remote computer system and the user portal can repeat this process—such as synchronized in time to the EEG test if played back at 1× speed or if viewed in real-time—until the user pauses or stops playback of the EEG test or until playback of the EEG test is completed. The user may thus visually interpret these tiles rendered sequentially on the display of her computing device as real-time or 1× playback of the EEG test.

In another example, the remote computer system generates and serves tiles to a user's client computing device responsive to a request to view EEG data from a live EEG test. In this example, the remote computer system can receive a set of sense signals—in the raw resolution—from the electroencephalography headset via a computer network in real-time during the electroencephalography test in Block S110. In Block S120, the remote computer system can receive a size of the viewport at the client computing device, a display resolution of the display in the client computing device, and a request for live access to the electroencephalography test from the client computing device in Block S120. The remote computer system can then execute Blocks of the method S100 described above to define a segment duration that is a fraction (e.g., one-fifth) of duration spanned by the full width of the viewport (e.g., 200 milliseconds for a one-section duration spanned by the viewport); and then calculate a first quantity of raw signal points in a sense signal per pixel column of the display based on the display resolution and the size of the viewport during approximately a first period of time that the electroencephalography headset recorded a first segment of each sense signal in Block S120. The remote computer system can then generate a first static image representing compressed segments of these signals in Block S150 and can transmit this first static image to the client computing device via the computer network at approximately the conclusion of the first period of time. The remote computer system can repeat this process responsive to receipt of each subsequent series of sense signal data spanning this segment duration or in response to receipt of a change in view parameters at the client computing device.

(In the implementation described above in which the remote computer system hosts post hoc playback of the EEG test at the user's client computing device, the remote computer system can implement similar methods and techniques to generate tiles that contain segments of compressed sense signals and that span less than the full width of the viewport. In this implementation, the remote computer system can generate and transmit each tile sequentially to the crossing confidence score. Alternatively, the remote computer system can generate a set of (e.g., five) tiles that together span the full width of the viewport in Block S150 and transmit this set of tiles to the client computing device in parallel in Block S160.)

Generally, Internet networks may not exhibit fully predictable characteristics. In order to reduce user-perceived effects of network jitter, the remote computer system can generate and serve tiles—representing current view parameters for the EEG test results—to the client computing device as rapidly as is supported by the remote computer system and by the network. The client computing device: can store tiles (e.g., five tiles) in a memory queue (e.g., a one-second buffer) before rendering tiles on the display of the computing device; and can render these tiles sequentially with a preset time offset between adjacent tiles (e.g., 200 milliseconds) in order to provide an impression of continuity in data rendered on the client computing device. To further improve perceived smoothness for rendering these tiles, the computing device can shift a sliding mask continuously across the display in order to obscure rigid boundaries between adjacent tiles.

8.3 Manual Scroll

In one implementation in which the user pauses automatic playback of live or post-hoc viewing of an EEG test, the remote computer system can selectively generate a next static image (or set of tiles) responsive to a manual input at the client computing device to scrub forward or in reverse through the EEG test.

For example, after serving a series of static images representing segments of compressed sense signals spanning a period of a selected EEG test, the user selects a virtual pause button within the user portal to cease automatic playback of the EEG test. Accordingly, the client computing device ceases returning queries to the remote computer system for next static images (or returns a query to cease transmission of next static images). Subsequently, when the user selects a virtual "scrub-forward" button in the user portal at a particular time to scrub forward to a particular timestamp within the EEG test, the client computing device can return a flag for a lateral scroll event to the particular timestamp in the EEG test to the client computing device via the computer network. Responsive to receipt of this flag for the lateral scroll event, the remote computer system can select a second segment of each active sense signal: spanning a duration of time calculated for static images according to current view parameters at the viewport; and including the particular timestamp in the EEG test. The remote computer system can then generate a next static image containing these second segments of compressed sense signals in Block S150 and return this next static image to the client computing device at approximately the particular time in Block S160.

In another example, when the user pauses playback of the EEG test at a current static image and before the user selects a scrub-forward or scrub-backward input at the user portal, the remote computer system: automatically generates a preceding static image representing segments of compressed sense signals spanning a period of time in the EEG test immediately preceding a period of time represented by the current static image; automatically generates a succeeding static image representing segments of compressed sense signals spanning a period of time in the EEG test immediately succeeding the period of time represented by the current static image; and transmits these preceding and succeeding static images to the client computing device for selective rendering based on whether the user selects the scrub-forward or scrub-backward input at the user portal. The remote computer system and the client computing device can therefore cooperate to "pre-fetch" or "pre-load" static images while waiting for the user to scrub forward, scrub backward, or resume automatic playback of the EEG test.

9. View Parameter Changes

The remote computer system can repeat the foregoing processes to generate each subsequent static image (or each subsequent set of tiles) spanning all or a fraction of the width of viewport and to serve each subsequent static image to the client computing device for rendering according to the last view parameters received from the client computing device.

In one example, the user portal can detect: a vertical scroll event; a horizontal scroll event; a zoom level change; activation and/or deactivation of a sense channel; resumption of playback of the EEG test; background or sense signal color change; reordering of sense signals; selection of a different compression method (e.g., standard deviation, maximum difference, average) for contiguous sequences of points in sense signals; etc. Upon detecting such a view parameter change event, the user portal can return this new view parameter value to the remote computer system, and the remote computer system can repeat processes described above to calculate a new compression level for sensor signals in the EEG test (i.e., a number of raw sense signal points per pixel) in Block S130, compress subsequent segments of sensor signals in the EEG test according to this new view parameter in Block S140, generate subsequent static images depicting subsequent segments of these compressed sense signals accordingly in Block S140, and return these static images to the client computing device in Block S160, as shown in FIG. 1.

The remote computer system can therefore immediately access inputs to modify current view parameters at the user portal in Block S120, remotely generate a next static image representing a next segment of the selected EEG test based on these new view parameters in Block S150, and immediately transmit this next static image to the client computing device for rendering in order to provide the user with a sense of real-time review control of these EEG data despite remote execution of analytics and image generation by the remote computer system.

10. User Annotations

In one variation, the remote computer system interfaces with the client computing device to record annotations entered by the user during playback of the EEG test at the user's client computing device. Generally, in this variation, the remote computer system interfaces with the client computing device to log placement, adjustment (e.g., via dragging), and editing of annotations within the viewport (e.g., over a sense, computed, or secondary channel depicted in a static image rendered within the viewport) and to link these annotations to specific times and/or to specific channels within the EEG test. In particular, once the user places an annotation in the viewport and the client computing device returns the annotation and a location of the annotation on a static image rendered in the viewport to the remote computer system, the remote computer system can convert the location of the annotation into EEG coordinates (e.g., into a timestamp and a sense, computed, or secondary channel within the EEG test).

In one implementation, the remote computer system receives, from the client computing device via the computer network: an annotation (e.g., a textual note, a flag or marker, an annotation icon from a dropdown menu) inserted by the user; a static image address of a static image previously generated by the remote computer system and rendered in the viewport at the time the annotation was inserted; and a pixel address of a pixel in the static image tagged with the annotation. The remote computer system then: identifies the static image as a particular static image based on the static image address; identifies a particular time segment (e.g., a 200-millisecond segment) within the EEG test depicted by the particular static image; isolates a particular time within this particular time segment corresponding to a horizontal value in the pixel address; isolates a particular channel in the EEG test responsive to a vertical position specified in the pixel address intersecting a particular section of the particular static image designated for the particular signal; and then stores the annotation reference to the EEG test, the particular channel, and the particular time. The remote computer system can repeat this process to transform and store other annotations entered by the user at the user portal during playback of the EEG test, and the remote computer system can compile these annotations into a time series of annotations synchronized to sense signals in the EEG test.

During subsequent playback of this EEG test at the same or other client computing device, the remote computer system can incorporate this time series of annotations entered by the user into a new secondary channel in a new sequence of static images generated for this next playback session of the EEG test and/or populate this new sequence of static images with synchronized annotations from these stored time series of annotations entered by the user.

11. Image Variation

In one variation, rather than generate and transmit individual static images depicting compressed segments of sense, computed, and/or secondary channels in Blocks S150 and S160, the remote computer system: compiles sequences of static images—generated according to a static set of view parameters—into a video file (e.g., spanning a one-second interval, spanning a five-second interval); transmits this video file to the client computing device for playback within the viewport; and repeats this process for subsequent sequences of static images based on view parameters at the user portal at corresponding times. In this variation, the client computing device can thus playback video segments depicting segments of the EEG test rather than individual static images (shown in FIG. 11).

The remote computer system can additionally or alternatively segment EEG data spanning the vertical height and horizontal width of the viewport (e.g., a set of channels and a period of the EEG test, respectively) into multiple vertical and horizontal tiles, as shown in FIG. 5.

12. Secondary Visualizations

In one variation, the remote computer system further generates secondary visualizations renderable within the user portal—such as within or adjacent the viewport—during playback of static images depicting the EEG test at the client computing device.

12.1 Spatial Heatmap

In one implementation, the remote computer system: calculates a spatial heatmap depicting amplitudes of signals detected by sense electrodes at known locations in the EEG headset—and therefore approximate known locations on the subjects scalp—at a particular instance in time concurrently depicted in a static image; overlays this spatial heatmap over a generic icon depicting a plan view of a subject's head to generate a secondary image; and serves this secondary image to the client computing device for rendering concurrently with a static image depicting segments of signals spanning a time period including this particular instance in time in Block S156, as shown in FIG. 11. In one example, the remote computer system calculates a spatial heatmap of amplitudes of a range of frequencies in the set of signals in the EEG test over the duration of the EEG test based on known locations of these sense electrodes in the EEG headset. During playback of the EEG test at the client computing device, the remote computer system: selects a next segment of the EEG test spanning a fraction of the duration of time depicted in the viewport; generates a heatmap image depicting the spatial heatmap at a particular time within (e.g., centered within) the fraction of the duration of time; generates a static image depicting segments of compressed sense signals spanning this fraction of the duration of time; and transmits the static image and heatmap image to the client computing device—via the computer network—for rendering substantially concurrently within the user portal.

In this implementation, the user portal can render a time marker—manually adjustable by the user—over the viewport, and the user portal can return a lateral position of the time marker to the remote computer system each time the user moves the time marker. The remote computer system can then: implement methods and techniques described above to transform the lateral position of the time marker into a time instance in the EEG test; generate a heatmap image depicting amplitudes of signals across the subject's scalp at this time instance in the EEG test; and then return this heatmap image to the client computing device for immediate rendering adjacent the viewport. The remote computer system can repeat the process as the time marker is moved within the viewport and/or as a static image moves relative to the time marker during automatic playback of the EEG test.

The remote computer system can also: generate a sequence of heatmap images depicting amplitudes of signals across the subject's scalp over a series of time instances in the EEG test; tag each of these heatmap images with a horizontal pixel location of a particular static image depicting signals at the corresponding time instance; and serve these to the client computing device. During playback of a static image depicting a compressed segment of the EEG test, the client computing device can: preload a set of heatmap images associated with this particular static image; track the lateral position of the time marker relative to the particular static image intersection in the viewport; and sequentially render each heatmap image—in the sequence of heatmap images—associated with a lateral pixel location equal to the current lateral position of the time marker. The client computing device can therefore render heatmap images time-synchronized to static images rendered in the viewport.

In a similar implementation, the remote computer system can; generate a sequence of heatmap images spanning time instances depicted in a static image; compile this sequence of heatmap images into a heatmap video file; and serve this heatmap video file—paired with the static image—to the client computing device in Block S160. The client computing device can then playback this heatmap video file within the user portal while concurrently rendering this static image in the viewport, such as according to a frame rate synchronized to a refresh rate or wipe rate of the static image moving into and out of the viewport. The remote computer system can therefore generate a heatmap video file depicting a spatial heatmap of signals depicted in one corresponding static image; and the client computing device can render this static image and playback this heatmap video file concurrently. However, the remote computer system can generate on heatmap video file depicting a spatial heatmap of signals depicted in multiple corresponding static images or serve spatial heatmap imagery to the client computing device in any other format for concurrent rendering with static images depicting the same sense signals in time-amplitude format.

12.2 Subject Video

In one implementation in which a video of a subject is recorded during the EEG test and is time-synchronized to sense signals recorded in the EEG test, the remote computer system can implement similar methods and techniques: to extract a series of individual frames from the video; to link each individual frame to a particular static image or to a particular pixel column or range of pixel columns in a particular static image; and to transmit this individual frame to the client computing device in Block S158. The client computing device can then render these individual frames adjacent the viewport based on which static image is currently rendered in the viewport and/or based on a position of a time marker in the viewport, as shown in FIG. 11.

Alternatively, the remote computer system can aggregate sequences of frames in the video into a set of subject video files, each containing frames recorded during a period of time represented by one (or a set) of static images; and the client computing device can replay these subject video files synchronized to rendering of corresponding static images in the viewport, as described above.

12. EEG Test Switching

The remote computer system can implement similar methods and techniques—in (near) real-time to load a second EEG test and to generate a sequence of images (or tiles) representing sense signals from this second EEG test and matched to current view parameters at the user portal in response to receipt of selection of this second EEG test at the user portal. The remote computer system can therefore enable the user to immediately switch between viewing two distinct EEG test results by eliminating a need for the user to download original sensor signals from these EEG tests to her computing device.

For example, the user may oversee EEG tests being recorded for multiple subjects concurrently at a hospital or clinic. As the user walks into a first room occupied by a first subject, the user may select the first subject's EEG test at the user portal, and the user portal can then cooperate with the remote computer system to receive and render static images—representing sense signals from the first subject's EEG test compressed according to current view parameters set by the user at the user portal—in (near) real-time. The user may later walk into a second room occupied by a second subject and then select the second subject's EEG test at the user portal accordingly. The user portal can then cooperate with the remote computer system to receive and render static images—representing sense signals from the second subject's EEG test compressed according to current view parameters set by the user at the user portal—in (near) real-time.

Alternatively, while collecting EEG test data from an EEG headset worn by the second user during this period of time, the remote computer system can analyze these EEG data and predict that the second subject is currently experiencing or about to experience a neurological abnormality (e.g., a seizure) and then serve a notification to the user portal to view this subject's EEG test results accordingly. (An EEG test administrator or technician overseeing the second subject can similarly send an electronic notification—indicating that the second subject is seizing or exhibiting another neurological abnormality—to the user via the user portal in order to prompt the user to switch to viewing the second subject's EEG test results.) The user can then select the second EEG test for viewing at the user portal, and the remote computer system can transition to supplying static images—representing sense signals from the second subject's EEG test compressed according to current view parameters set by the user at the user portal—to the user portal.

In the foregoing example, the remote computer system can also enable the user to switch between viewing such EEG test results of multiple subjects remotely via the user portal. The remote computer system can also execute the foregoing Blocks of the method S100 to serve compressed sense signal data for a single EEG test of one subject to multiple instances of the user portal accessed by multiple users simultaneously, such as according to unique combinations of view parameters set at each of these user portals.

The remote computer system can implement similar methods and techniques to serve EEG test data for multiple distinct EEG tests (e.g., of the same subject or different subjects) to the user portal simultaneously, such as to enable the user to compare these different EEG tests side-by-side without downloading raw sense signals from both EEG tests directly to her computing device.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for hosting mobile access to dense electroencephalography data comprising, at a computer system:
    receiving a first signal, in a raw resolution, recorded by a first channel in an electroencephalography headset during an electroencephalography test executed on the electroencephalography headset;
    receiving, from a client computing device, a size of a viewport rendered on a display of the client computing device and a display resolution of the display;
    calculating a duration of time encompassed by the viewport based on the size of the viewport and the display resolution;
    selecting a first segment of the first signal spanning a fraction of the duration of time;
    initializing a first static image;
    calculating a first quantity of raw signal points in the first signal per pixel column of the first static image based on the display resolution, the size of the viewport, and a time length of the first segment of the first signal;
    for each discrete contiguous sequence of the first quantity of raw signal points within the first segment of the first signal:
        extracting a minimum value from the discrete contiguous sequence of raw signal points;
        extracting a maximum value from the discrete contiguous sequence of raw signal points;
        calculating an average of the discrete contiguous sequence of raw signal points; and
        calculating a standard deviation of the discrete contiguous sequence of raw signal points;
        representing the minimum value, the maximum value, the average, and the standard deviation in a set of color values in pixels in a pixel column of the first static image, the pixel column corresponding to a time window spanned by the discrete contiguous sequence of the first quantity of raw signal points within the first segment of the first signal;
    transmitting the first static image to the client computing device, via a computer network, for rendering;
    generating a second static image representing a second segment of the first signal succeeding the first segment; and
    transmitting the second static image to the client computing device for rendering within the viewport.

2. The method of claim 1:
    wherein receiving the first signal comprises:
        at the remote computer system remote from the electroencephalography headset, receiving the first signal, in the raw resolution, streamed from the electroencephalography headset in real-time during the electroencephalography test; and
        storing the first signal in a remote database;
    wherein transmitting the first static image to the client computing device comprises transmitting the first static image to the client computing device, comprising a mobile computing device with limited network and computing bandwidth carried by a user, via a wired or wireless network.

3. The method of claim 1:
    wherein receiving the first signal comprises downloading the first signal, in the raw resolution, from the electroencephalography headset via the computer network in real-time during the electroencephalography test;
    wherein receiving the size of the viewport and the display resolution of the display comprises receiving the size of the viewport, the display resolution of the display, and a request for live access to the electroencephalography test from the client computing device;
    wherein calculating the first quantity of raw signal points in the first signal per pixel column of the display comprises calculating the first quantity of raw signal points in the first signal per pixel column of the display based on the display resolution and the size of the viewport during approximately a first period of time that the electroencephalography headset recorded the first segment of the first signal;
    wherein initializing the first static image comprises generating the first static image at approximately a conclusion of the first period of time; and
    wherein transmitting the first static image to the client computing device comprises transmitting the first static image to the client computing device via the computer network at approximately the conclusion of the first period of time.

4. The method of claim 1:
    wherein receiving the first signal comprises downloading the first signal, in the raw resolution, from the electroencephalography headset via the computer network over a first period of time;
    wherein receiving the size of the viewport and the display resolution comprises receiving, from the client computing device at a second time succeeding the first period of time, a width dimension of the viewport rendered on the display, the display resolution of the display, a zoom level selected at the viewport, and a first timestamp in the electroencephalography test selected for viewing at the viewport;
    further comprising:
        transforming the width dimension of the viewport and the zoom level into a duration of time encompassed by the viewport at the second time; and
        selecting the first segment of the first signal spanning the duration of time and comprising the first timestamp in the electroencephalography test;

wherein transmitting the first static image to the client computing device comprises transmitting the first static image to the client computing device at approximately the second time;
further comprising:
at a third time succeeding the second time, receiving, from the client computing device, a flag for a lateral scroll event to a second timestamp in the electroencephalography test; and
responsive to the flag for the lateral scroll event, selecting the second segment of the first signal spanning the duration of time and comprising the second timestamp in the electroencephalography test; and
wherein transmitting the second static image to the client computing device comprises transmitting the second static image to the client computing device at approximately the third time.

5. The method of claim 1:
wherein receiving the size of the viewport and the display resolution comprises receiving, from the client computing device, a width dimension of the viewport rendered on the display, the display resolution of the display, and a zoom level selected at the viewport;
further comprising:
transforming the width dimension of the viewport and the zoom level into a duration of time encompassed by the viewport; and
selecting the first segment of the first signal spanning a fraction of the duration of time;
further comprising:
selecting the second segment of the first signal spanning the fraction of the duration of time and immediately succeeding the first segment of the first signal; and
for each discrete contiguous sequence of the first quantity of raw signal points within the second segment of the first signal:
extracting a second minimum value from the discrete contiguous sequence of raw signal points;
extracting a second maximum value from the discrete contiguous sequence of raw signal points;
calculating a second average of the discrete contiguous sequence of raw signal points; and
calculating a second standard deviation of the discrete contiguous sequence of raw signal points; and
representing the second minimum value, the second maximum value, the second average, and the second standard deviation in the set of color values in pixels in a second pixel column of the first static image, the second pixel column corresponding to a second time window spanned by the discrete contiguous sequence of the first quantity of raw signal points within the second segment of the first signal; and
wherein transmitting the first static image and transmitting the second static image to the client computing device comprises streaming the first static image and second static image to the client computing device over the computer network, the first static image and the second static image renderable within the viewport as columnar tiles depicting the first signal over the duration of time.

6. The method of claim 5, further comprising, at the client computing device:
storing the first static image and the second static image in a local buffer; and
on a regular interval during playback of the electroencephalography test at the client computing device:
removing a rightmost static image rendered in the viewport;
indexing remaining static image rendered in the viewport leftward by a width of each static image; and
inserting a next sequential static image, stored in the local buffer, into a leftmost position within the viewport.

7. The method of claim 1:
wherein representing the minimum value, the maximum value, the average, and the standard deviation for each discrete contiguous sequence of the first quantity of raw signal points along the first segment of the first signal in the first static image comprises, for each discrete contiguous sequence of the first quantity of raw signal points along the first segment of the first signal:
generating a column of pixels representing the minimum value, the maximum value, the average, and the standard deviation of the discrete contiguous sequence of raw signal points; and
locating the column of pixels at a location within the first static image corresponding to a time period within the electroencephalography test represented by the discrete contiguous sequence of raw signal points.

8. The method of claim 7, wherein generating the column of pixels representing the minimum value, the maximum value, the average, and the standard deviation of the discrete contiguous sequence of raw signal points comprises:
defining the column of pixels in a first color and spanning the minimum value and the maximum value of the discrete contiguous sequence of raw signal points;
shifting a first subset of pixels, in the column of pixels, corresponding to values between the average and a low side of the standard deviation of the discrete contiguous sequence of raw signal points from the first color to a second color; and
shifting a second subset of pixels, in the column of pixels, corresponding to values between the average and a high side of the standard deviation of the discrete contiguous sequence of raw signal points from the first color to a third color.

9. The method of claim 7, wherein initializing the first static image comprises:
retrieving a background image for electroencephalography tests, the background image depicting a chart and a time label on a horizontal axis of the chart;
scaling the background image based on a duration of the first segment of the first signal, a size of a viewport, and a zoom level selected at the viewport; and
for each discrete contiguous sequence of the first quantity of raw signal points along the first segment of the first signal, locating the column of pixels representing the discrete contiguous sequence of raw signal points over a first section of the background image associated with the first channel.

10. The method of claim 1:
further comprising, at the remote computer system:
scanning the first segment of the first signal for a subsegment representing an artifact; and
generating a processed waveform representing the first segment of the first signal with the subsegment attenuated;

wherein representing the minimum value, the maximum value, the average, and the standard deviation for each discrete contiguous sequence of the first quantity of raw signal points along the first segment of the first signal in the first static image comprises representing each discrete contiguous sequence of the first quantity of raw signal points along the first segment of the first signal with pixels in a first color set over a first section of a background image associated with the first channel; and further comprising representing the processed waveform with pixels in a second color set over the first section of the background image.

11. The method of claim 10:

further comprising, at the remote computer system, scanning the first segment of the first signal for a subsegment indicating a period of poor contact quality between a first sense electrode that recorded the first signal and skin of a patient wearing the electroencephalography headset during an electroencephalography test; and wherein representing the minimum value, the maximum value, the average, and the standard deviation for each discrete contiguous sequence of the first quantity of raw signal points along the first segment of the first signal in the first static image comprises:

representing each discrete contiguous sequence of the first quantity of raw signal points along the first segment of the first signal, excluding the subsegment, with pixels in a first color set in the first static image; and representing each discrete contiguous sequence of the first quantity of raw signal points within the subsegment of the first signal with pixels in a second color set in the first static image to indicate detection of poor contact quality.

12. The method of claim 1:

further comprising, at the remote computer system:

downloading a second signal, in the raw resolution, recorded by a second channel in the electroencephalography headset concurrently with the first signal during the electroencephalography test;

for each discrete contiguous sequence of the first quantity of raw signal points within a first segment of the second signal:

extracting a second minimum value from the discrete contiguous sequence of raw signal points;

extracting a second maximum value from the discrete contiguous sequence of raw signal points;

calculating a second average of the discrete contiguous sequence of raw signal points; and calculating a second standard deviation of the discrete contiguous sequence of raw signal points;

representing the second minimum value, the second maximum value, the second average, and the second standard deviation in the set of color values in pixels in a second pixel column in a second section of the first static image associated with the second channel, the second pixel column corresponding to a second time window spanned by the discrete contiguous sequence of the first quantity of raw signal points within the first segment of the second signal;

wherein representing the minimum value, the maximum value, the average, and the standard deviation for each discrete contiguous sequence of the first quantity of raw signal points along the first segment of the first signal in the first static image comprises representing each discrete contiguous sequence of the first quantity of raw signal points along the first segment of the first signal in a first section of the first static image associated with the first channel; and further comprising, at the remote computer system:

accessing a key image comprising a first icon and a second icon, the first icon depicting a first location of a first sense electrode on the electroencephalography headset that recorded the first signal, the second icon depicting a second location of a second sense electrode on the electroencephalography headset that recorded the second signal;

scaling the key image based on the size of the viewport to align the first icon with the first section of the first static image and to align the second icon with the second section of the first static image; and transmitting the key image to the client computing device for rendering within the viewport concurrently with and adjacent the first static image.

13. The method of claim 1:

wherein downloading the first signal comprises downloading a set of signals, in the raw resolution and comprising the first signal, recorded by a set of sense electrodes in the electroencephalography headset during the electroencephalography test;

further comprising, for each signal in the set of signals excluding the first signal:

selecting a segment of the signal spanning a duration of time during the electroencephalography test queued for rendering within the viewport; and for each discrete contiguous sequence of the first quantity of raw signal points within the segment of the signal:

extracting a second minimum value from the discrete contiguous sequence of raw signal points;

extracting a second maximum value from the discrete contiguous sequence of raw signal points;

calculating a second average of the discrete contiguous sequence of raw signal points; and calculating a second standard deviation of the discrete contiguous sequence of raw signal points; and representing the second minimum value, the second maximum value, the second average, and the second standard deviation in the set of color values in pixels in a second pixel column of the first static image, the second pixel column corresponding to a second time window spanned by the discrete contiguous sequence of the first quantity of raw signal points within the segment of the signal;

further comprising, at the remote computer system:

aggregating the set of signals into a composite signal; and calculating a temporal heatmap of amplitudes of a range of frequencies within the composite signal; and wherein representing the minimum value, the maximum value, the average, and the standard deviation for each discrete contiguous sequence of the first quantity of raw signal points along the first segment of the first signal in the first static image comprises:

for each signal in the set of signals, representing discrete contiguous sequences of the first quantity of raw signal points along the segment of the signal within a horizontal section of the first static image corresponding to a sense electrode, in the set of sense electrodes, that recorded the signal during the electroencephalography test; and further comprising representing a segment of the temporal heatmap corresponding to the duration of time in a horizontal section of the first static image assigned to the composite signal and vertically aligned with horizontal sections of the first static image corresponding to the set of sense electrodes.

14. The method of claim 13:

further comprising:
downloading a time series of annotations input by a technician viewing a patient wearing the electroencephalography headset during the electroencephalography test;
downloading a time series of photic flashes output by a strobe proximal the patient during the electroencephalography test;

further comprising:
populating the first static image with a technician flag containing a textual annotation extracted from a first segment of the time series of annotations corresponding to the duration of time and temporally aligned to horizontal sections of the first static image corresponding to the set of sense electrodes; and
representing the time series of photic flashes in a horizontal section of the first static image assigned to a photic channel and vertically aligned with horizontal sections of the first static image corresponding to the set of sense electrodes.

15. The method of claim 1:

wherein receiving the size of the viewport and the display resolution comprises receiving, from the client computing device at a first time, a width dimension of the viewport rendered on the display, the display resolution of the display, and a first zoom level selected at the viewport;

further comprising:
transforming the width dimension of the viewport and the first zoom level into a first duration of time encompassed by the viewport at the first time; and
selecting the first segment of the first signal spanning the first duration of time;

wherein transmitting the first static image to the client computing device comprises transmitting the first static image to the client computing device at approximately the first time;

wherein generating the second static image comprises, in response to absence of a change from the first zoom level at the viewport from the first time to a second time, generating the second static image representing a second segment of the first signal succeeding the first segment and spanning the first duration of time;

wherein transmitting the second static image to the client computing device comprises transmitting the second static image to the client computing device at approximately the second time; and further comprising:
receiving, from the client computing device at a third time succeeding the second time, a second zoom level selected at the viewport;
transforming the width dimension of the viewport and the second zoom level into a second duration of time encompassed by the viewport at the third time;
selecting a third segment of the first signal spanning the third duration of time and succeeding the second segment;

calculating a third quantity of raw signal points in the first signal per pixel column of the display based on the display resolution, the size of the viewport, and a length of the third segment of the first signal;

for each discrete contiguous sequence of the third quantity of raw signal points within the third segment of the first signal:
extracting a third minimum value from the discrete contiguous sequence of raw signal points;
extracting a third maximum value from the discrete contiguous sequence of raw signal points;
calculating a third average of the discrete contiguous sequence of raw signal points; and
calculating a third standard deviation of the discrete contiguous sequence of raw signal points; and
representing the third minimum value, the third maximum value, the third average, and the third standard deviation in the set of color values in pixels in a third pixel column of a third static image, the third pixel column corresponding to a third time window spanned by the discrete contiguous sequence of the third quantity of raw signal points within the third segment of the first signal; and transmitting the third static image to the client computing device at approximately the third time.

16. The method of claim 1, further comprising:

receiving, from the client computing device via the computer network:
an annotation;
a static image address of a static image; and
a pixel address of a pixel in the static image tagged with the annotation by a user at the client computing device;

identifying the static image as the first static image based on the static image address;

identifying a particular time segment within the electroencephalography test depicted by the first static image;

isolating a particular time within the particular time segment corresponding to a horizontal value in the pixel address;

isolating the first channel responsive to a vertical position specified in the pixel address intersecting a first section of the first static image associated with the first signal; and storing the annotation referenced to the electroencephalography test, the first channel, and the particular time.

17. A method for hosting mobile access to dense electroencephalography data comprising:

over a first period of time:
downloading a first sequence of raw signal points recorded during an EEG test executed on an electroencephalography headset, the first sequence of raw signal points read from a first sense channel in the electroencephalography headset during the first period of time;
receiving a request to view data from the first sense channel within a viewport rendered on a display of a client computing device, a display resolution of the display, a size of the viewport from the client computing device, and a zoom level within the viewport;
initializing a first static image;
calculating a first quantity of raw signal points per pixel column of the first static image based on the display resolution, the size of the viewport, and the zoom level;

for each discrete contiguous sequence of the first quantity of raw signal points in the first sequence of raw signal points:
extracting a minimum value from the discrete contiguous sequence of raw signal points;
extracting a maximum value from the discrete contiguous sequence of raw signal points;
calculating an average of the discrete contiguous sequence of raw signal points; and
calculating a standard deviation of the discrete contiguous sequence of raw signal points;
representing the minimum value, the maximum value, the average, and the standard deviation in a set of color values in pixels in a pixel column of the first static image, the pixel column corresponding to a time window spanned by the discrete contiguous sequence of the first quantity of raw signal points in the first sequence of raw signal points;
transmitting the first static image to the client computing device, via a computer network, for rendering within the viewport; and
over a second period of time immediately succeeding the first period of time:
downloading a second sequence of raw signal points from the electroencephalography headset, the second sequence of raw signal points read from the first sense channel during the second period of time;
for each discrete contiguous sequence of the first quantity of raw signal points in the second sequence of raw signal points, compressing the discrete contiguous sequence of the second quantity of raw signal points into a value set;
generating a second static image representing value sets of discrete contiguous sequences of the second quantity of raw signal points along the second sequence of raw signal points; and
transmitting the second static image to the client computing device for rendering within the viewport adjacent and succeeding the first static image.

18. A method for hosting mobile access to dense electroencephalography data comprising:
receiving a set of signals, in a raw resolution, recorded by a set of channels in an electroencephalography headset during an electroencephalography test executed on the electroencephalography headset;
receiving, from a client computing device, a size of a viewport rendered on a display of the client computing device and a display resolution of the display;
calculating a first quantity of raw signal points per pixel column of the display based on the display resolution, the size of the viewport, and a length of a first segment of the electroencephalography test;
for each signal in the set of signals:
for each discrete contiguous sequence of the first quantity of raw signal points within the first segment of the signal:
extracting a minimum value from the discrete contiguous sequence of raw signal points;
extracting a maximum value from the discrete contiguous sequence of raw signal points;
calculating an average of the discrete contiguous sequence of raw signal points; and
calculating a standard deviation of the discrete contiguous sequence of raw signal points;
representing the minimum value, the maximum value, the average, and the standard deviation in a set of color values in pixels in a pixel column of the first static image, the pixel column corresponding to a time window spanned by the discrete contiguous sequence of the first quantity of raw signal points within the first segment of the signal;
transmitting the first static image to the client computing device, via a computer network, for rendering.

19. The method of claim 18:
wherein receiving the size of the viewport and the display resolution comprises receiving, from the client computing device, a width dimension of the viewport rendered on the display, the display resolution of the display, and a zoom level selected at the viewport; and
further comprising:
transforming the width dimension of the viewport and the zoom level into a duration of time encompassed by the viewport; and
selecting the first segment of the electroencephalography test spanning a first fraction of the duration of time;
calculating a spatial heatmap of amplitudes of a range of frequencies in the set of signals based on known locations of the set of sense electrodes in the electroencephalography headset;
generating a second static image depicting the spatial heatmap at a particular time within the first fraction of the duration of time; and
transmitting the second static image to the client computing device, via the computer network, for rendering within the viewport substantially concurrently with and adjacent the first static image.

20. The method of claim 18:
further comprising, for each signal in the set of signals excluding the first signal:
for each discrete contiguous sequence of the first quantity of raw signal points along the first segment of the signal:
generating a column of pixels representing the minimum value, the maximum value, the average, and the standard deviation of the discrete contiguous sequence of raw signal points; and
locating the column of pixels at a location within the first static image corresponding to a time period within the electroencephalography test represented by the discrete contiguous sequence of raw signal points.

* * * * *